US012631648B2

(12) United States Patent
Chatterjee et al.

(10) Patent No.: US 12,631,648 B2
(45) Date of Patent: May 19, 2026

(54) COMPOUNDS FOR THE DETECTION OF HOMOCYSTEINE AND ITS METHOD OF PREPARATION THEREOF

(71) Applicant: Council of Scientific & Industrial Research, New Delhi (IN)

(72) Inventors: Pabitra Baran Chatterjee, Bhavnagar (IN); Snehasish Debnath, Bhavnagar (IN); Ratish Rajgopalan Nair, Bhavnagar (IN)

(73) Assignee: Council of Scientific & Industrial Research, New Delhi (IN)

( * ) Notice: Subject to any disclaimer, the term of this patent is extended or adjusted under 35 U.S.C. 154(b) by 589 days.

(21) Appl. No.: 18/024,376

(22) PCT Filed: Sep. 3, 2021

(86) PCT No.: PCT/IN2021/050849

§ 371 (c)(1),
(2) Date: Mar. 2, 2023

(87) PCT Pub. No.: WO2022/049598

PCT Pub. Date: Mar. 10, 2022

(65) Prior Publication Data

US 2024/0011998 A1 Jan. 11, 2024

(30) Foreign Application Priority Data

Sep. 5, 2020 (IN) ............................ 202011038506

(51) Int. Cl.
*G01N 33/00* (2006.01)
*C07F 1/08* (2006.01)
*G01N 33/68* (2006.01)

(52) U.S. Cl.
CPC ........... *G01N 33/6815* (2013.01); *C07F 1/08* (2013.01)

(58) Field of Classification Search
CPC ................................................. G01N 33/6815
(Continued)

(56) References Cited

U.S. PATENT DOCUMENTS

2016/0077103 A1 3/2016 Strongin et al.

FOREIGN PATENT DOCUMENTS

WO WO 2015/200692 12/2015

OTHER PUBLICATIONS

Chao et al., "Aggregation enhanced luminescent detection of homocysteine in water with terpyridine-based $Cu^{2+}$ complexes" *Sens. Actuat. B* 2017, 245, 146-155.

(Continued)

*Primary Examiner* — Elizabeth A Robinson
*Assistant Examiner* — Emily R. Berkeley
(74) *Attorney, Agent, or Firm* — Norton Rose Fulbright US LLP

(57) ABSTRACT

The present invention discloses compounds of Formula-A and its copper complex of general Formula-B. The compound of general Formula-B is used in the selective detection of homocysteine in aqueous medium at physiological pH without any interference from other challenging amino acids and thiols. Using compounds of general Formula-B, specific detection of homocysteine under UV light in aqueous solution is also possible by the naked eyes.

(Continued)

Formula-A

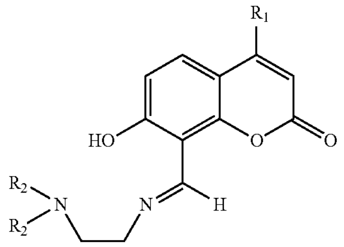

Formula-B

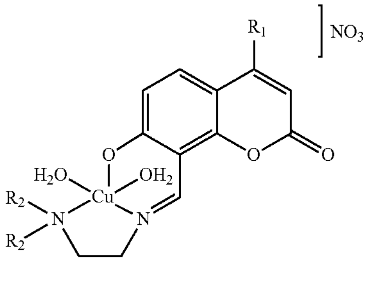

7 Claims, 16 Drawing Sheets

(58) Field of Classification Search
USPC ........................................................... 436/90
See application file for complete search history.

(56) References Cited

OTHER PUBLICATIONS

Chen et al., "Selective Phosphorescence Chemosensor for Homocysteine Based on an Iridium(III) Complex" *Inorg. Chem.* 2007, 46, 11075-11081.
Gao et al., "Aldehyde bearing bis-cyclometalated Ir(III) complex as selective photoluminescence turn-on probe for imaging intracellular homocysteine" *Sens. Actuat. B* 2017, 245, 853-859.
Hakuna et al., "A photochemical method for determining plasma homocysteine with limited sample processing" *Chem. Commun.* 2014, 50, 3071-3073.
He et al., "Synthesis of a fluorogenic probe for thiols based on a coumarin Schiff base copper complex and its use for the detection of glutathione" Tetrahedron 2016, 1-6.
Kong et al., "A highly sensitive near-infrared fluorescent probe for cysteine and homocysteine in living cells" *Chem. Commun.* 2013, 49, 9176-9178.
Kovac et al., "Liquid Chromatography-Tandem Mass Spectrometry Method for Determination of Homocysteine in Rat Plasma: Application to the Study of a Rat Model for Tauopathies" *J. Chromatographic Sci.* 2014, 53(6), 953-958.
Li et al., "BODIPY-based azamacrocyclic ensemble for selective fluorescence de-tection and quantification of homocysteine in biological applications" *Biosens. Bioelectron.* 2015, 72, 1-9.
Rusin et al., "Visual Detection of Cysteine and Homocysteine" *J. Am. Chem. Soc.* 2004, 126, 438-439.
Sun et al., "A sensitive and selective resonance light scattering bioassay for homocysteine in biological fluids based on target-involved assembly of polyethyleneimine-capped Ag-nanoclusters" *Chem. Commun.* 2011, 47, 3817-3819.
Tang et al., "A coumarin derivative as a "turn-on" fluorescence probe toward $Cd^{2+}$ in live cells" *Spectrochimica Acta Part A: Molecular and Biomolecular Spectroscopy* 2019, 218, 359-365.
Wang et al., "A coumarin-based dual optical probe for homocysteine with rapid response time, high sensitivity and selectivity" *Talanta* 2019, 196, 243-248.
Wang et al., "Aldehyde-functionalized Metal-organic Framework for Selective Sensing of Homocysteine over Cys, GSH and Other Natural Amino Acids" *Chem. Commun.* 2018, 54, 1004-1007.
Wang et al., "Direct Detection of Homocysteine" *J. Am. Chem. Soc.* 2004, 126, 3400-3401.
Yeon Lee et al., "Selective homocysteine turn-on fluorescent probes and their bioimaging applications" *Chem. Commun.* 2014, 50, 6967-6969.

COMPOUNDS FOR THE DETECTION OF HOMOCYSTEINE AND ITS METHOD OF PREPARATION THEREOF

CROSS-REFERENCE TO RELATED APPLICATIONS

This application is a national phase application under 35 U.S.C. § 371 of International Application No. PCT/IN2021/050849 filed 3 Sep. 2021, which claims priority to Indian Patent Application number 202011038506 filed 5 Sep. 2020. The entire contents of each of the above-referenced disclosures is specifically incorporated herein by reference without disclaimer.

FIELD OF THE INVENTION

The present invention relates to a copper complex of Formula B. Particularly, present invention also relates to a process for the preparation of Formula B. More particularly, present invention relates to copper complex of Formula B which is highly efficient to detect the amino acid homocysteine in aqueous medium at physiological pH (7 to 7.5). The fluorimetric detection of homocysteine by Formula-B is not hindered by other amino acids and glutathione.

Formula-B

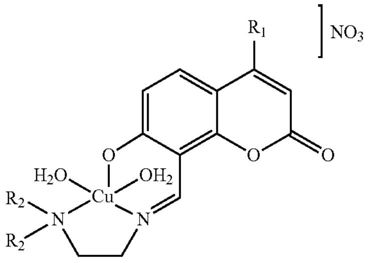

BACKGROUND OF THE INVENTION

Homocysteine (Hcy) is a sulfur containing amino acid, which functions as a metabolite of the amino acid methionine. Hcy along with other biological thiols like cysteine (Cys) and glutathione (GSH), plays crucial role in a wide ranges of physiological and pathological processes, including protein structure and function, redox homeostasis, detoxification, and metabolism. Hcy being a sulfur based amino acid, is susceptible to oxidation at physiological pH, forming disulfides with other thiols. Thus, in plasma, trace amount (1%) of Hcy exists in the reduced form. Approximately, 70% of total Hcy is bound with albumin and remaining 30% forms low molecular weight disulfides predominantly, with Cys. If the sum of all Hcy, i.e. total Hcy (tHcy) exceeds≥15 μM in plasma, it is termed as hyperhomocysteinemia (HHcy).

Over the last 10 years, HHcy has been considered as one of the possible marker for the onset of cardiovascular diseases (CVD), brain atrophy, cognitive impairment, dementia, Alzheimer's disease (AD), etc. HHcy doubled the risk factor of dementia leading to Alzheimer's disease in aged person. Mild cognitive impairment (MCI) is an early stage of cognitive decline in the continuum from normal aging to dementia and it may progress to AD. With time, the prevalence and economic costs of AD are increasing with increasing number of old peoples. It has been estimated that nearly 25 million people worldwide currently have dementia and it is going to be worsen as the disease progresses with time. Hence, effective diagnostic kit is required for use in the early stage of cognitive impairment, which can prevent disease progression from MCI to AD.

Recently, HHcy has emerged as a cardiovascular risk factor by the American Heart Association. Cardiovascular disease (CVD) is believed to be one of the world's deadly disease and this disease causes about 30% of the annual worldwide deaths. The first sign of heart disease, in 25% of the adults, is sudden death from heart attack and nowadays CVD is most common among the youths. An elevated level of Hcy in the blood causes narrowing and hardening of the arteries that leads to diminished blood flow through the affected arteries. Eventually, lack of blood supply to the heart causes heart attacks. As a result, demand for plasma Hcy testing got increased momentum, perhaps explosively. Since Hcy is a homologue of Cys, differing only by an additional methylene moiety, selective detection/measurement of Hcy in human blood plasma is a very challenging task due to the interference from cysteine and glutathione.

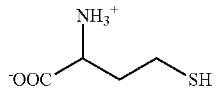

Homocysteine (Hey)

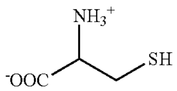

Cysteine (Cys)

Reference may be made to the patent WO2015200692A2, wherein the inventors have disclosed a method of fluorimetric detection of Hcy over other biothiols using a dansyl azide based probe. The major drawback of the system is the use of organic solvent (10% ethanol) to make the dye soluble. Also, high concentration requirement of the dye (120 μM) is also necessary for the selective detection of Hcy.

Reference may be made to the patent US20160077103A1, wherein the inventors disclosed a method of developing a probe, which is capable of undergoing condensation/cyclisation reaction with Hcy/Cys and thus, can selectively detect Hcy and Cys by the fluorescence emission. Requirement of 20% organic solvent (ethanol) to dissolve the probe mark its limitations. Again, the requirement of excitation wavelength $\lambda_{ex}$=304 nm makes it unsuitable for cell imaging application.

Reference may be made to an article by Weihua Wang et al. published in J. Am. Chem. Soc. 2004, 126, 3400-3401, wherein they have disclosed a colorimetric method using methyl viologen solution that showed response in presence of Hcy at neutral pH. The major drawback of the system is the requirement of high concentration of Hcy (17 mM) for colorimetric detection. Also, high amount of organic solvent (70% methanol) is necessary for the detection.

Reference may be made to an article by Oleksandr Rusin et al. published in J. Am. Chem. Soc. 2004, 126, 438-439, wherein they have reported a method for detection of Cys and Hcy using a xanthene dye. The major drawback of the system is the interference of Cys during the detection of Hcy. Again, requirement of alkaline pH (9.5) condition makes it incompatible for biological studies.

Reference may be made to an article by Huili Chen et al. published in Inorg. Chem. 2007, 46, 11075-11081, wherein they have disclosed a phosphorescence sensor based on Iridium complex for Hcy. High amount of organic solvent and cost of the probe makes it inappropriate for clinical studies.

Reference may be made to an article by Shao-Kai Sun et al. published in Chem. Commun. 2011, 47, 3817-3819, wherein the authors have disclosed resonance light scattering (RLS) based bioassay utilizing polyethyleneimine (PEI)-capped Ag-nanoclusters for detecting Hcy in biological fluids. The major drawback of the system is the enhancement of RLS intensity in the pH regime 4-6. Therefore, the system is not useful at physiological pH condition.

Reference may be made to an article by Fanpeng Kong et al. published in Chem. Commun. 2013, 49, 9176, wherein they have disclosed a cyanine7 based near-infrared probe for the detection of endogenous Cys/Hcy in living cells. The major drawback of this system is the interference of Cys in the detection of Hcy.

Reference may be made to an article by Hye Yeon Lee et al. published in Chem. Commun. 2014, 50, 6967-6969, wherein the authors have disclosed a pyrene based fluorescent probe for the detection of Hcy. The major drawback of the system is the use of 10% organic solvent (DMSO) to make the probe soluble for performing required experiments.

Reference may be made to an article published by Andrej Kovac et al. in the J. Chromatographic Sci. 2014, 53(6), 953-958, wherein they have disclosed a liquid chromatography-tandem mass spectrometry method for determination of Hcy in rat plasma. Use of sophisticated instruments, pre-treatment of the sample, and tedious technique are the major drawbacks of the work.

Reference may be made to an article by Lovemore Hakuna et al. published in Chem. Commun. 2014, 50, 3071-3073, wherein they have disclosed a method of assaying Hcy in human plasma using methyl viologen and benzyl viologen as probes. Requirement of higher concentration of the probes (50 mM and 20 mM of methyl viologen and benzyl viologen, respectively) for the assay is the major limitation of the system.

Reference may be made to an article by Zan Li et al. published in Biosens. Bioelectron. 2015, 72, 1-9, wherein they have disclosed a BODIPY-based azamacrocyclic ensemble containing $Cu^{2+}$ for the fluorimetric detection and quantification of Hcy. Several steps in the synthetic route and cost of BODIPY are the major drawbacks.

Reference may be made to an article by Duobin Chao et al. published in Sens. Actuat. B 2017, 245, 146-155, wherein the authors have disclosed a method for the selective detection of Hcy using 4 different terpyridine based Cu complexes. Tedious synthetic route and low yield of its Cu complexes are the major drawback.

Reference may be made to an article by Hongfang Gao et al. published in Sens. Actuat. B 2017, 245, 853-859, wherein they have disclosed a new probe for the selective detection of Hcy. Use of costly iridium salt and organic solvent are the major limitations.

Reference may be made to an article by Jian Wang et al. published in Chem. Commun. 2018, 54, 1004-1007, wherein the authors have disclosed an aldehyde functionalized porous MOF that can act as a sensor for discriminating Hcy from other natural amino acids. The major drawback of this system is the use of suspension of Cd-PPCA (1H-Pyrrolo [2,3-b]pyridine-2-carbaldehyde).

Reference may be made to an article by Kun-Peng Wang et al. published in Talanta. 2019, 196, 243-248, wherein they have disclosed a dual optical probe based on coumarin dimer for selective recognition of Hcy. Use of 50% DMSO makes this probe inappropriate for biological studies.

OBJECTIVES OF THE INVENTION

Main objective of the present invention is to provide a compound of Formula B. Another objective of the present invention is to provides a process for the preparation of a series of compounds of Formula B.

Yet another objective of the present invention is to provide a compound of Formula B useful for the selective detection of homocysteine in water solution at physiological pH (7 to 7.5).

Yet another objective of the present invention is to use compound of Formula B for the selective recognition of homocysteine in water solution at physiological pH (7 to 7.5) via turn-on fluorosense response, which is also observable by the naked eyes under UV lamp (365 nm).

SUMMARY OF THE INVENTION

Accordingly, present invention provides a compound of Formula B

Formula-B

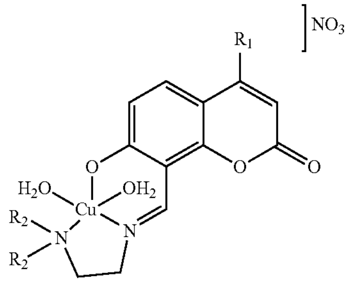

wherein $R_1$=—$CH_3$ or —H and $R_2$=—$CH_3$ or —$C_2H_5$.

In an embodiment of the present invention, compound of formula B is selected from the group consisting of:

i. [Diaqua-8-(2-dimethylamino)ethyl)minomethyl-7-phenoxo-4-methyl-2H-chromen-2-onecopper(II) nitrate]

Compound 5

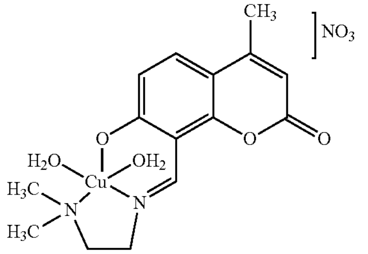

ii. [Diaqua-8-(2-(diethylamino)ethyliminomethyl-7-phenoxo-4-methyl-2H-chromen-2-onecopper(II) nitrate]

Compound 6

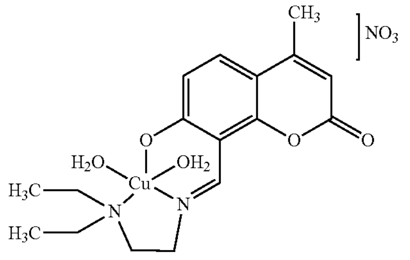

iii. [Diaqua-8-(2-(dimethylamino)ethyliminomethyl-7-phenoxo-2H-chromen-2-onecopper(II) nitrate]

Compound 7

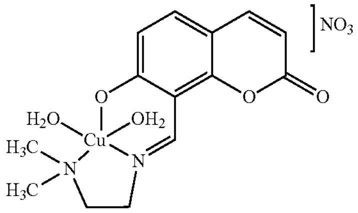

iv. [Diaqua-8-(2-(diethylamino)ethyliminomethyl-7-phenoxo-4-2H-chromen-2-onecopper(II) nitrate]

Compound 8

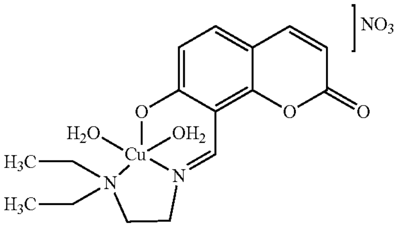

In another embodiment, present invention provides a process for the preparation of the compounds of Formula B comprising the steps of:

(i) refluxing a mixture of 7-Hydroxy-4-methyl-2-oxo-2H-chromene-8-carbaldehyde or 7-Hydroxy-2-oxo-2H-chromene-8-carbaldehyde and N,N-dimethylethylenediammine or N,N-diethylethylenediammine in a stoichiometry ratio 1:1 in a solvent for a period in the range of 3-4 h followed by evaporating the solvent to obtain a residue;

(ii) triturating the residue as obtained in step (i) with diethyl ether to get a yellow solid;

(iii) recrystallizing the solid as obtained in step (ii) to obtain crystalline Compound of Formula-A;

Formula-A

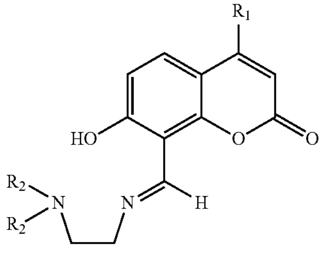

(iv) refluxing a mixture of copper salt and compound of Formula A in 1:1 stoichiometry in a solvent for a period in the range of 3-4 h followed by evaporating the solvent to obtain green coloured solid;

(v) filtering the green coloured solid as obtained in step (i) followed by drying to obtain a solid;

(vi) recrystallizing the solid as obtained in step (ii) to obtain compound of Formula-B in pure form.

In yet another embodiment of the present invention, compound of formula A is selected from the group consisting of:

i. [8-(2-(Dimethylamino)ethyl)minomethyl)-7-hydroxy-4-methyl-2H-chromen-2-one];

Compound 1

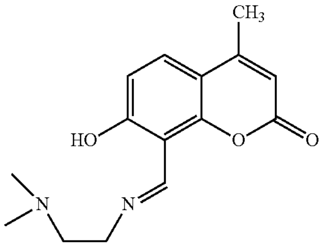

ii. [8-(2-(Diethylamino)ethyliminomethyl-7-hydroxy-4-methyl-2H-chromen-2-one

Compound 2

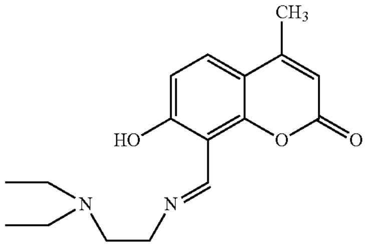

iii. [8-(2-(Dimethylamino)ethyliminomethyl-7-hydroxy-2H-chromen-2-one]

Compound 3

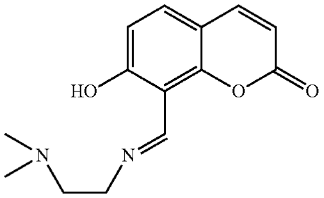

iv. [8-(2-(Diethylamino)ethyl)minomethyl-7-hydroxy-2H-chromen-2-one]

Compound 4

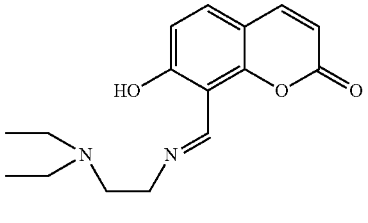

In yet another embodiment of the present invention, solvent used is selected from methanol or acetonitrile.

In yet another embodiment of the present invention, the copper salts used is selected from the group consisting of copper nitrate trihydrate, copper halide, copper perchlorate or copper acetate.

In yet another embodiment of the present invention, said compound are used for the fluorimetric measurement of Hcy in aqueous solution at physiological pH (7 to 7.5), even in presence of other competing species such as alanine, methionine, threonine, proline, leucine, isoleucine, lysine, phenylalanine, hydroxyproline, asparagine, argenine, serine, valine, cysteine, glutathione (reduced), glycine, histidine, and glutamine.

DETAIL DESCRIPTION OF THE INVENTION

Present invention provides compound of Formula A and its copper complex of Formula B. The present invention provides a general process for the preparation of compound of Formula-A by reacting 7-hydroxy-4-methyl-2-oxo-2H-chromene-8-carbaldehyde or 7-Hydroxy-2-oxo-2H-chromene-8-carbaldehyde with stoichiometric (1:1) amount of N,N-dimethylethylenediammine or N,N-diethylethylenediammine in methanol.

The present invention provides a process for the preparation of compound of Formula B by reacting stoichiometric amount (1:1) of compound of Formula A with different copper salts such as copper nitrate/copper halide/copper perchlorate/copper acetate in methanol or acetonitrile.

The present invention provides a process for the synthesis of Compound 1 comprising the steps of:

(i) 7-Hydroxy-4-methyl-2-oxo-2H-chromene-8-carbaldehyde (204 mg, 1 mmol) and N,N-dimethylethylenediamine (88 mg, 1 mmol) in 1:1 stoichiometry were dissolved in 15 mL methanol and refluxed for ca. 3-4 h;

(ii) residue as obtained in step (i) was triturated with diethyl ether after evaporating the solvent using rotary evaporator to get a yellow solid;

(iii) recrystallization of the yellow solid from diethyl ether resulted crystalline Compound 1.

Figure 1:
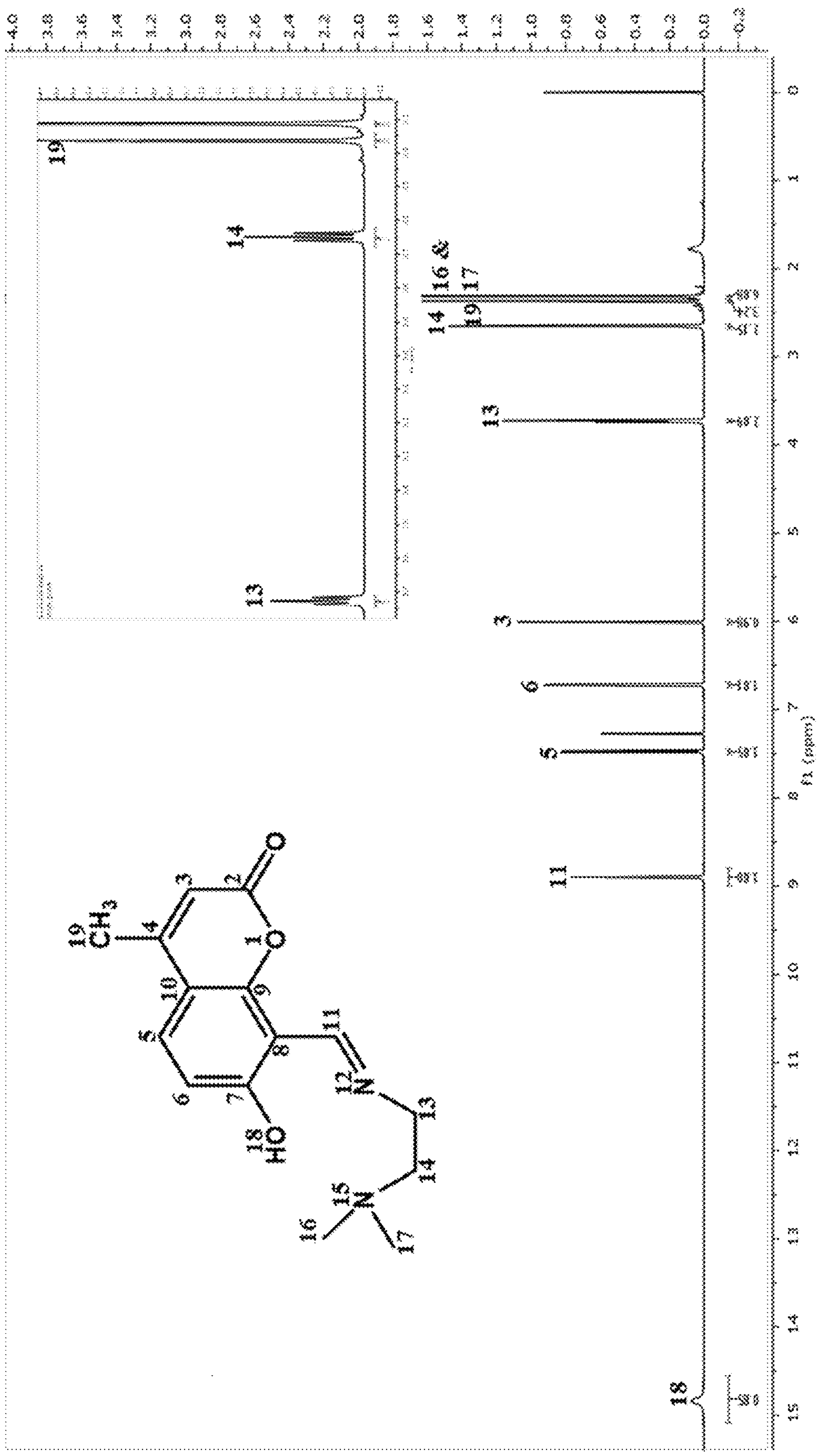
FIG. 1. $^1$H NMR spectrum of Compound 1.
Figure 5:
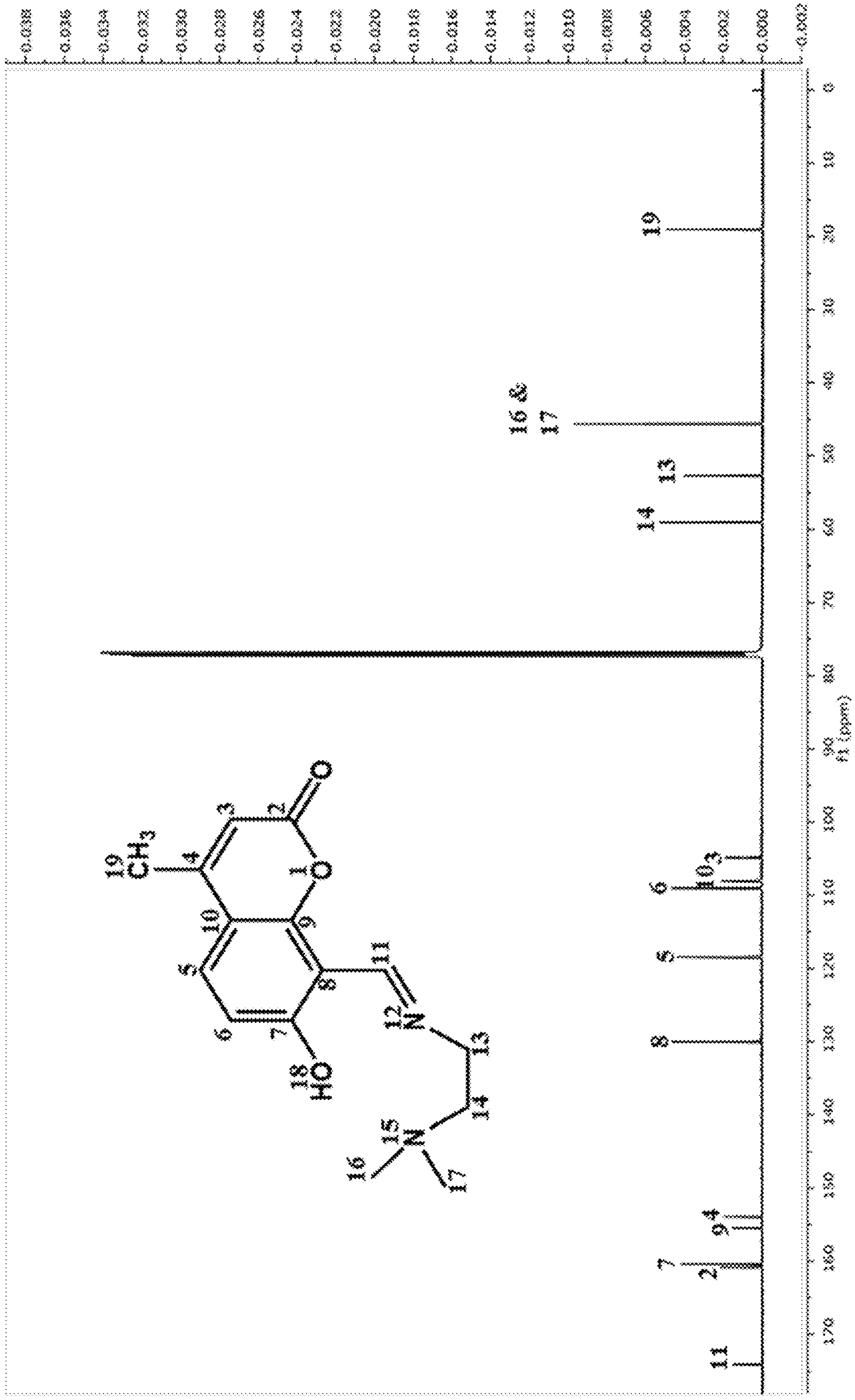
FIG. 5. $^{13}$C NMR spectrum of Compound 1.

In the present invention, both $^1$H (FIG. 1) and $^{13}$C NMR (FIG. 5) confirms the preparation of Compound 1.

The invention provides a process for the synthesis of Compound 2 comprising the steps of:

(i) 7-Hydroxy-4-methyl-2-oxo-2H-chromene-8-carbaldehyde (204 mg, 1 mmol) and N,N-diethylethylenediamine (116 mg, 1 mmol) in 1:1 stoichiometry was refluxed in 15 mL methanol for ca. 3-4 h;

(ii) residue as obtained in step (i) was triturated with diethyl ether after evaporating the solvent to get a brownish yellow solid;

(iii) recrystallization of the brownish yellow solid from diethyl ether resulted crystalline Compound 2.

Figure 2:
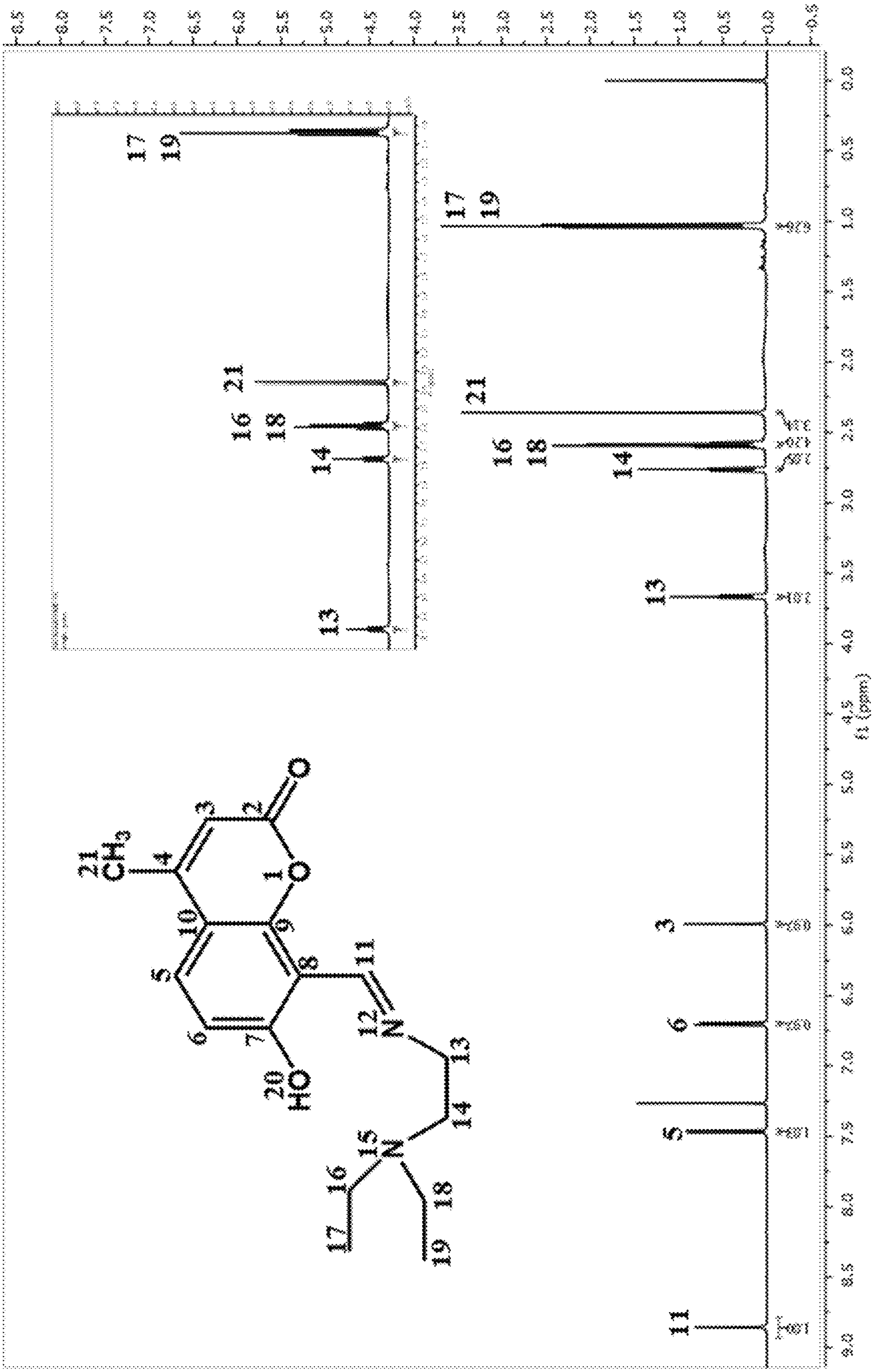
FIG. 2. $^1$H NMR spectrum of Compound 2.
Figure 6:
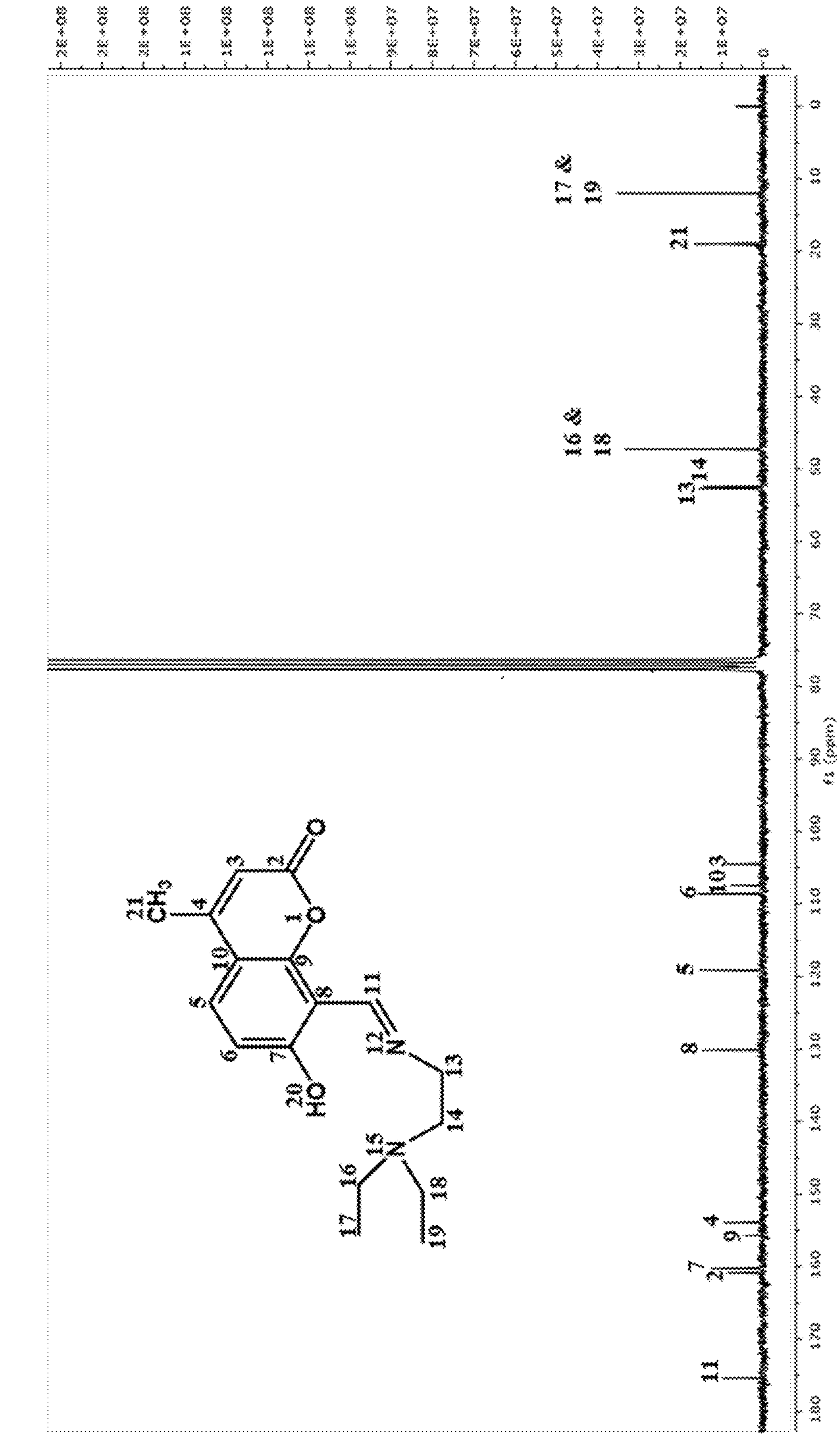
FIG. 6. $^{13}$C NMR spectrum of Compound 2.

In the present invention, both $^1$H (FIG. 2) and $^{13}$C NMR (FIG. 6) confirms the preparation of Compound 2.

The invention provides a process for the synthesis of Compound 3 comprising the steps of:

(i) 7-Hydroxy-2-oxo-2H-chromene-8-carbaldehyde (190 mg, 1 mmol) and N,N-dimethylethylenediamine (88 mg, 1 mmol) in 1:1 stoichiometry was refluxed in 15 mL methanol for ca. 3-4 h;

(ii) residue as obtained in step (i) was triturated with diethyl ether after evaporating the solvent to get a yellow solid;

(iii) recrystallization of the yellow solid from diethyl ether resulted crystalline Compound 3.

Figure 3:
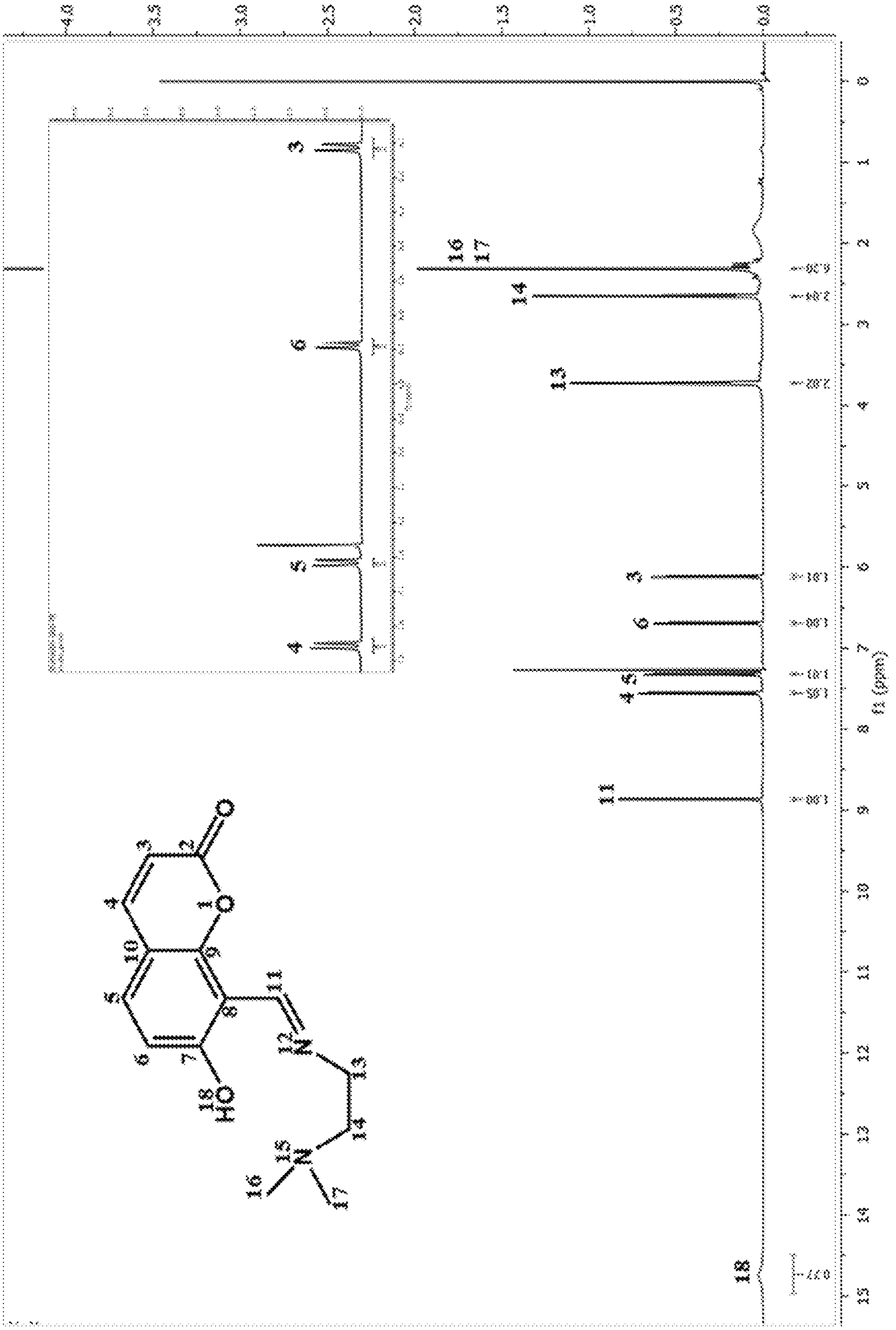
FIG. 3. $^1$H NMR spectrum of Compound 3.
Figure 7:
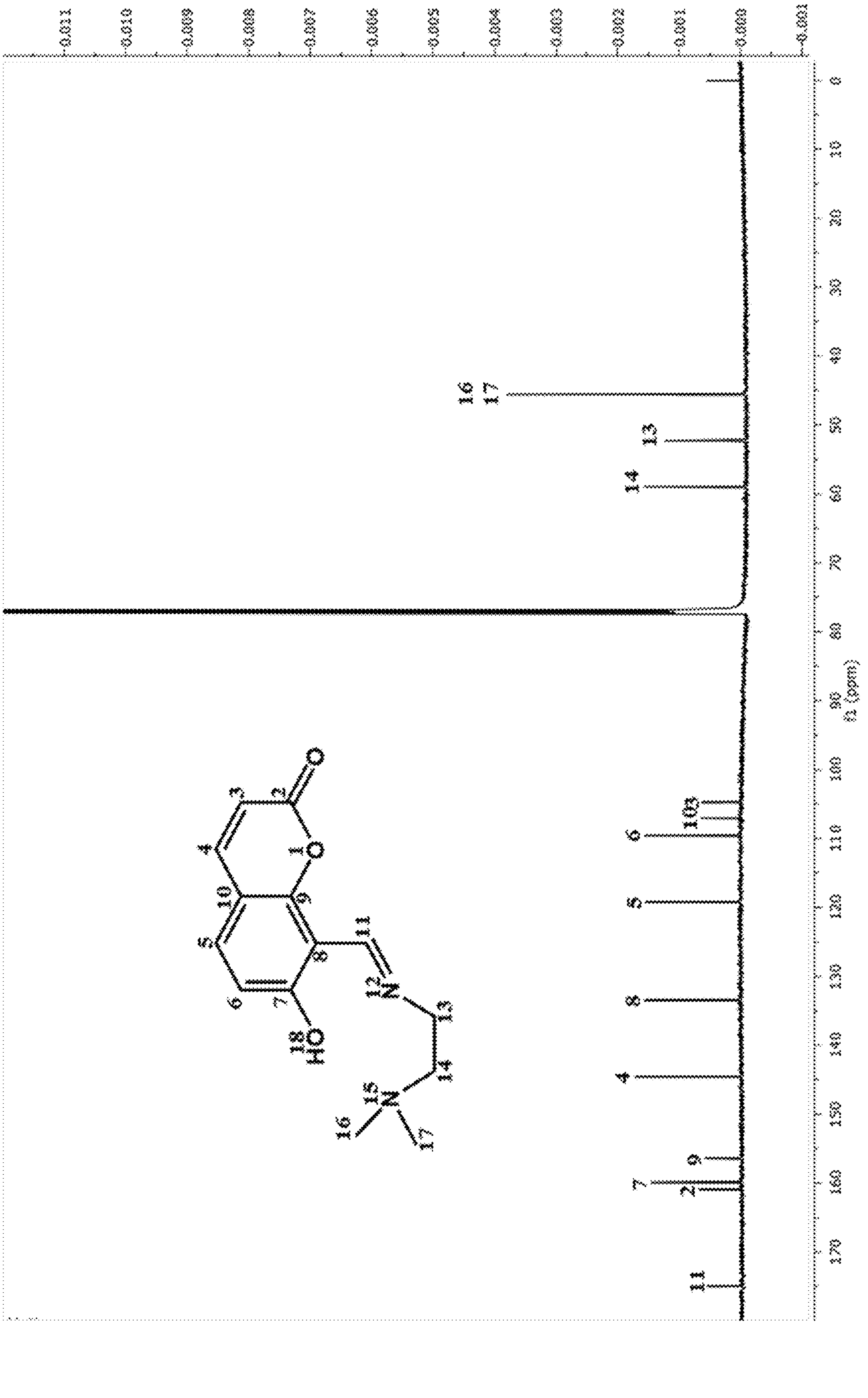
FIG. 7. $^{13}$C NMR spectrum of Compound 3.

In the present invention, both $^1$H (FIG. 3) and $^{13}$C NMR (FIG. 7) confirms the preparation of Compound 3.

The invention provides a process for the synthesis of Compound 4 comprising the steps of:

(i) 7-Hydroxy-2-oxo-2H-chromene-8-carbaldehyde (190 mg, 1 mmol) and N,N-diethylethylenediamine (116 mg, 1 mmol) in 1:1 stoichiometry was refluxed in 15 mL methanol for ca. 3-4 h;

(ii) residue as obtained in step (i) was triturated with diethyl ether after evaporating the solvent to get a brownish residue;

(iii) recrystallization of the brownish solid from diethyl ether resulted crystalline Compound 4.

Figure 4:
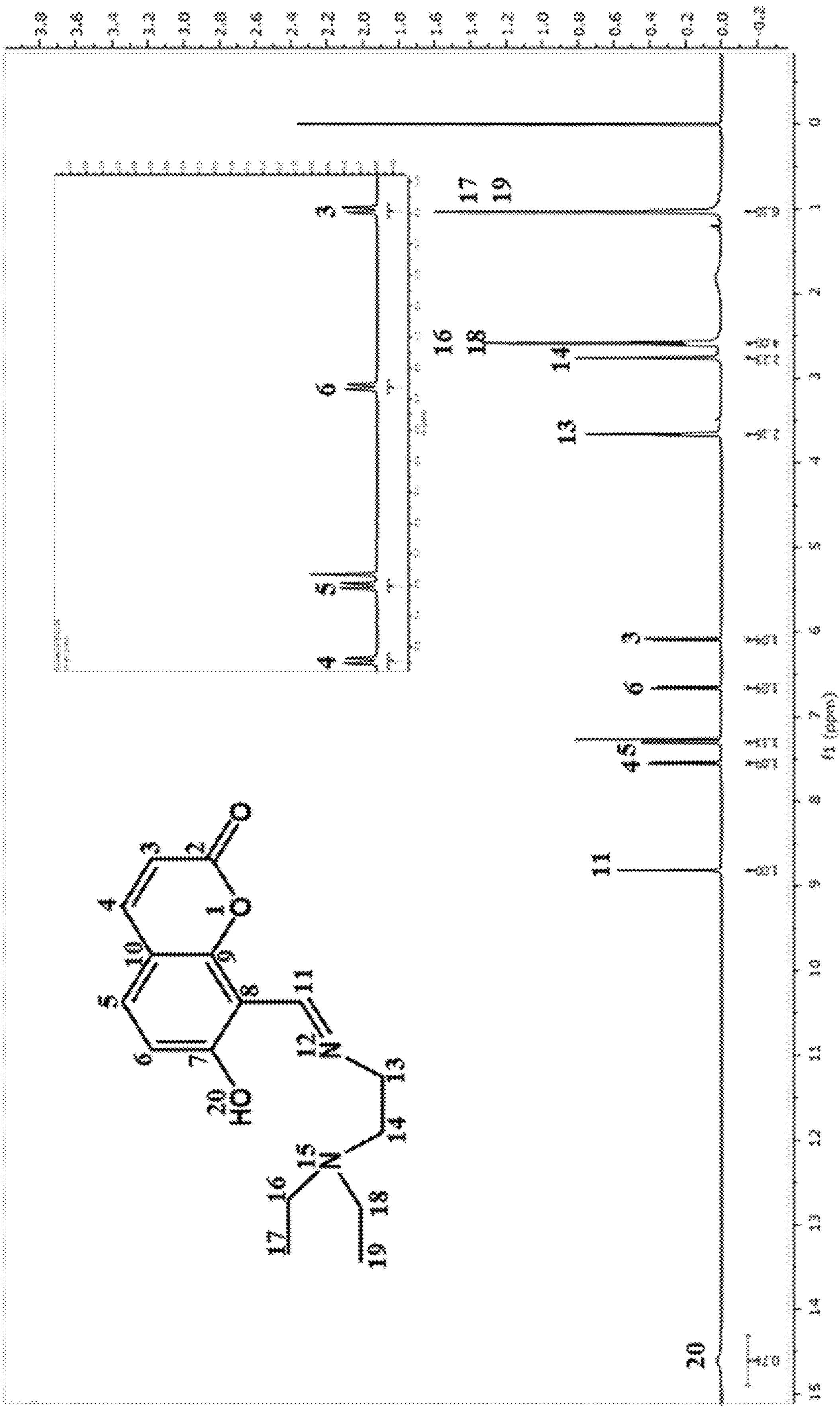
FIG. 4. $^1$H NMR spectrum of Compound 4.
Figure 8:
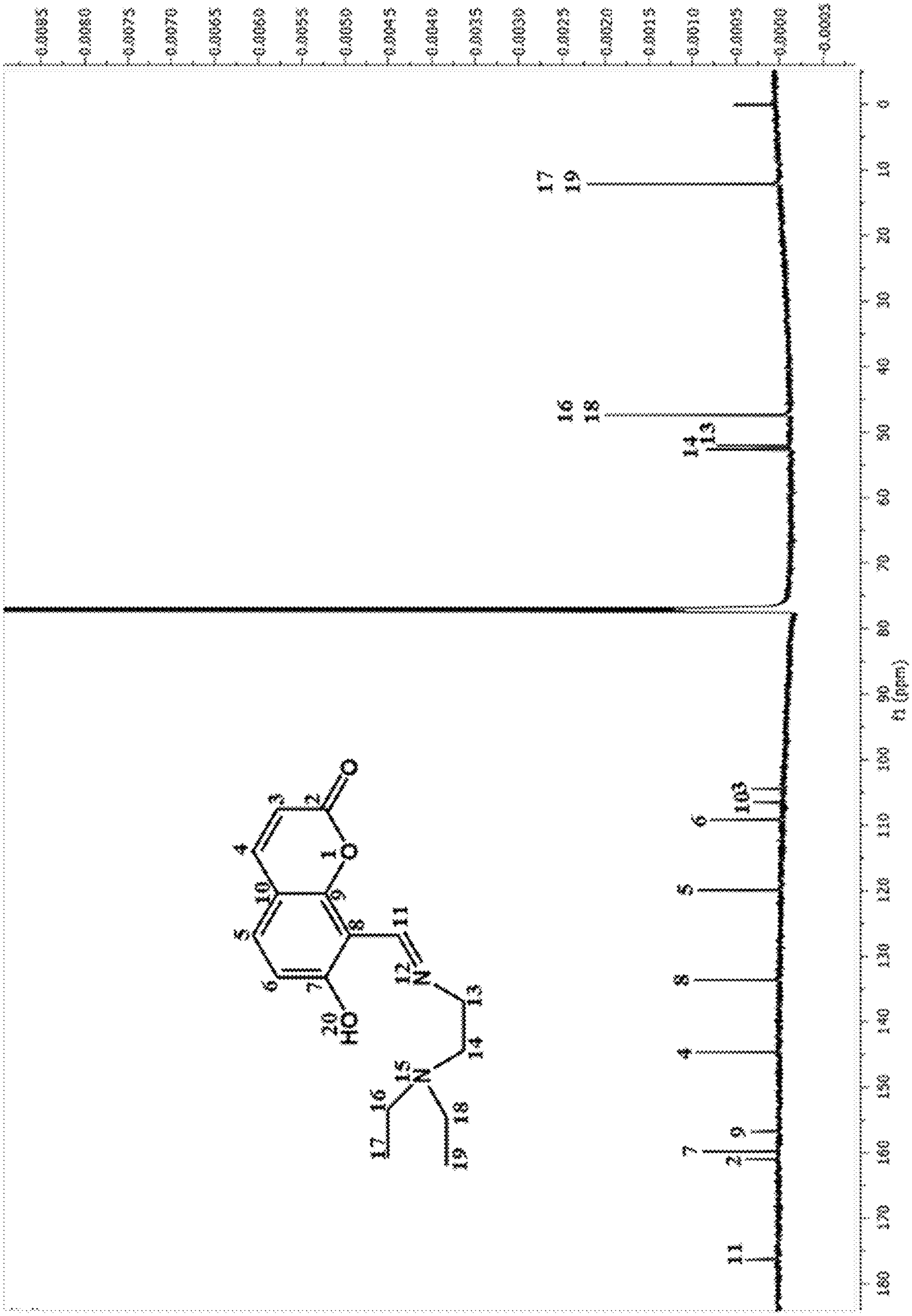
FIG. 8. $^{13}$C NMR spectrum of Compound 4.

In the present invention, both $^1$H (FIG. 4) and $^{13}$C NMR (FIG. 8) confirms the preparation of Compound 4.

The invention provides a process for the synthesis of Compound 5 comprising the steps of:

(i) a mixture of copper nitrate trihydrate (241.6 mg, 1 mmol) and Compound 1 (274 mg, 1 mmol) in 1:1 stoichiometry was refluxed in methanol solution (30 mL) for ca. 3-4 h;

(ii) green solid precipitated at the bottom of the round bottom flask, was obtained by evaporating half of the solvent, which was filtered and the residue was dried in a desiccator;

(iii) recrystallization from methanol solution produced crystalline Compound 5.

The invention provides a process for the synthesis of Compound 6 comprising the steps of:

(i) A mixture of copper nitrate trihydrate (241.6 mg, 1 mmol) and Compound 2 (302 mg, 1 mmol) in 1:1 stoichiometry was refluxed in methanol solution (30 mL) for ca. 3-4 h;

(ii) green at the bottom of the round bottom flask, was obtained by evaporating half of the solvent, which was filtered and the residue was collected and dried in a desiccator;

(iii) recrystallization from methanol solution resulted deep green Compound 6.

The invention provides a process for the synthesis of Compound 7 comprising the steps of:

(ii) A mixture of copper nitrate trihydrate (241.6 mg, 1 mmol) and Compound 3 (260 mg, 1 mmol) in 1:1 stoichiometry was refluxed in methanol solution (30 mL) for ca. 3-4 h;

(iii) deep green solid precipitated at the bottom of the round bottom flask, was obtained by evaporating half of the solvent, which was filtered and the residue was dried in a desiccator;

(iv) recrystallization from methanol solution resulted green powder of Compund 7.

The invention provides a process for the synthesis of Compound 8 comprising the steps of:

(i) A mixture of copper nitrate trihydrate (241.6 mg, 1 mmol) and Compound 4 (288 mg, 1 mmol) in 1:1 stoichiometry was refluxed in methanol solution (30 mL) for ca. 3-4 h;

(ii) deep green solid at the bottom of the round bottom flask was obtained by evaporating half of the solvent, which was filtered and dried in a desiccator;

(iii) recrystallization from methanol solution produced green powder of Compound 8.

In the present invention, a fluorimetric process for the selective recognition of Homocysteine (Hcy) using the Compounds 5 to 8 in aqueous solution at physiological pH (7 to 7.5) has been developed.

Fluorescence enhancement at 439 nm of Compounds 5 to 8 (20 μM) was observed on addition of Hcy solution, which was monitored via emission technique upon exciting the solution at 370 nm (slit width, 2 nm).

Fluorescence intensity enhancement of the mixtures of Compounds 5 to 8 (20 μM) and equivalent each of different amino acids such as L-glycine, L-alanine, L-leucine, L-isoleucine, L-valine, L-glutamine, L-lysine, L-proline, L-hydroxyproline, L-phenylalanine, L-aspargine, L-serine, L-threonine, L-histidine, L-arginine, L-aspartic acid, L-glutamic acid, L-methionine, L-cysteine, and L-glutathione (reduced) was studied in HEPES buffer (10 mM) at physiological pH (7 to 7.5). The mixtures were excited at 370 nm (slit width, 2 nm) and the emission spectra were recorded between 380 and 580 nm in the liquid mode after 1 h incubation of the mixture. Selective detection of Hcy by Compounds 5 to 8 without any interference from the other competing amino acids was noticed.

Turn on fluorescence response of Compounds 5 to 8 (20 μM) in HEPES buffer (10 mM) at physiological pH (7 to 7.5) was perceived by the naked eyes under UV lamp (360 nm) in presence of Hcy.

Spectrofluorimetric titration of Compounds 5 to 8 against Hcy was carried out upon excitation at 370 nm (slit width, 2 nm). Non-linear fitting of the data points corresponding to the maximum emission intensity at 439 nm (Compounds 5 and 6) and 445 nm (Compounds 7 and 8) yielded binding constant $1.75\times10^3$, $2.15\times10^3$, $1.23\times10^3$, and $1.68\times10^3$ $M^{-1}$, respectively for Compounds 5, 6, 7, and 8. Lower detection limit (LOD) was found to be 15, 2.5, 12, and 8 μM for Compounds 5, 6, 7, and 8 respectively.

Figure 9:
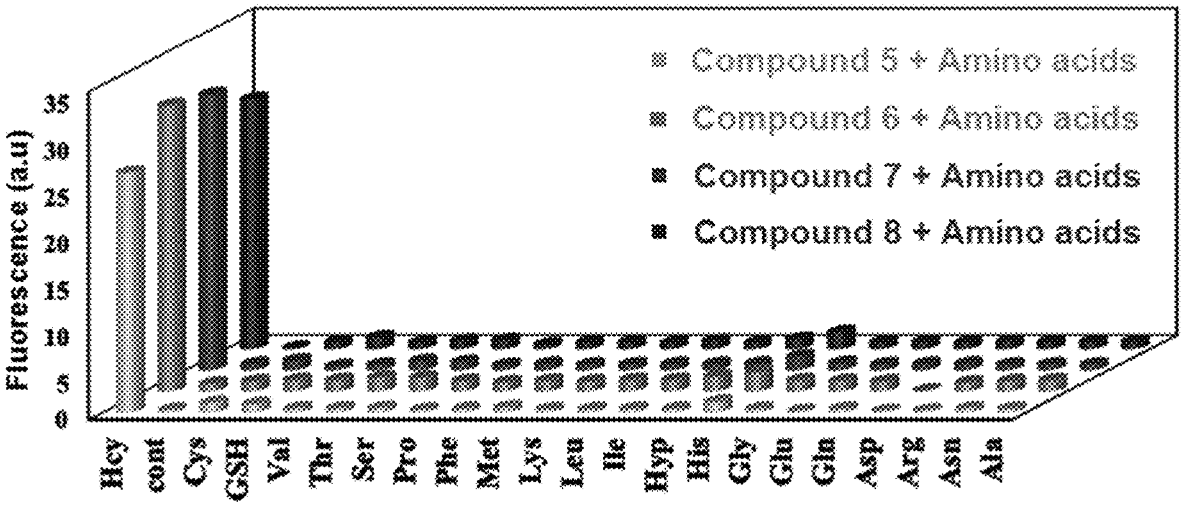
FIG. 9. Fluorimetric responses of 20 μM Compounds 5 to 8 toward 25 equivalents of different amino acids, upon excitation at 370 nm (slit width, 2 nm) at physiological pH (7.4).
Figure 10:
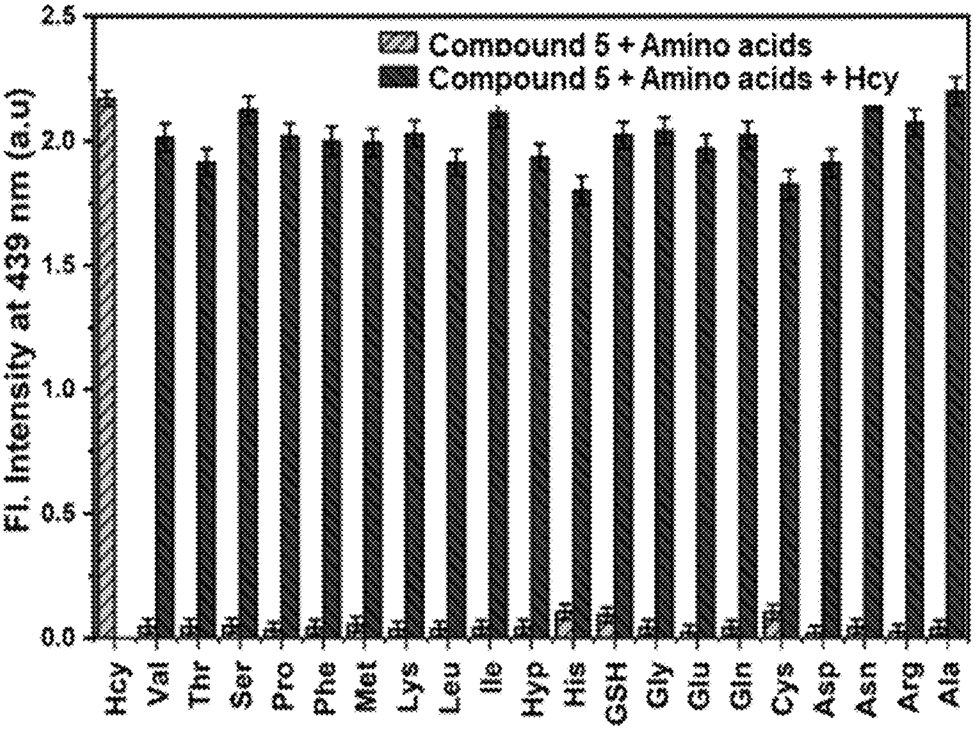
FIG. 10. Bar diagram showing selective fluorescence turn on responses of Compound 5 (20 μM in HEPES buffer) with Hcy (25 equivalent) in presence of equivalent amount of other competing amino acids.
Figure 11:
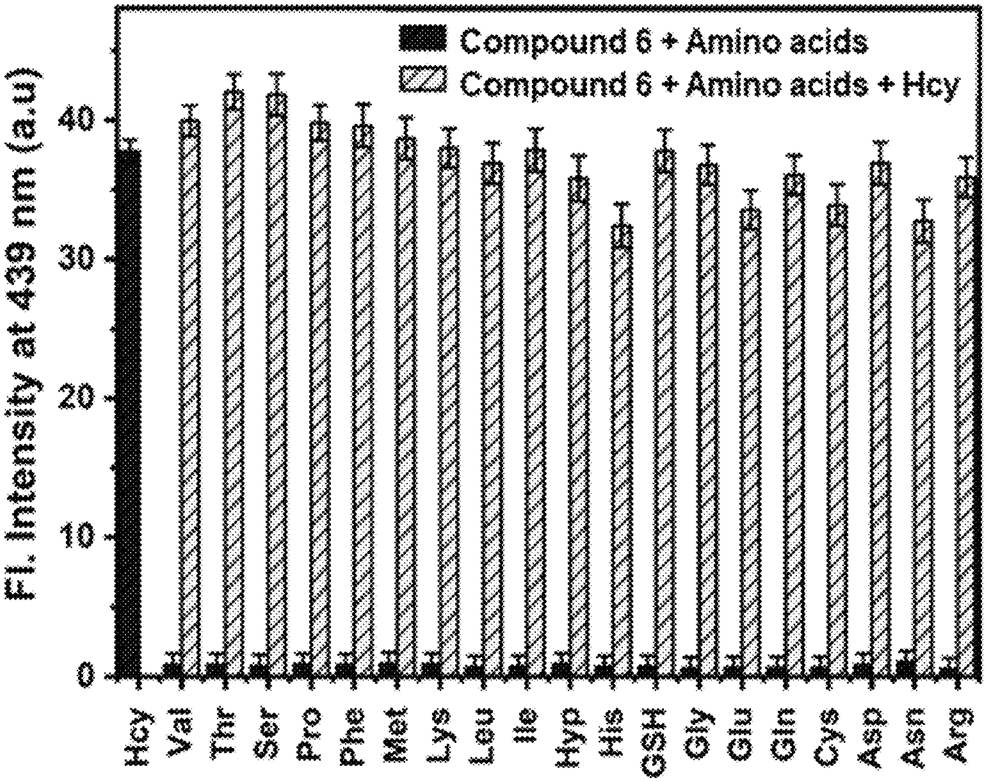
FIG. 11. Bar diagram showing selective fluorescence turn on responses of Compound 6 (20 μM in HEPES buffer) with Hcy (25 equivalent) in presence of equivalent amount of other competing amino acids.
Figure 12:
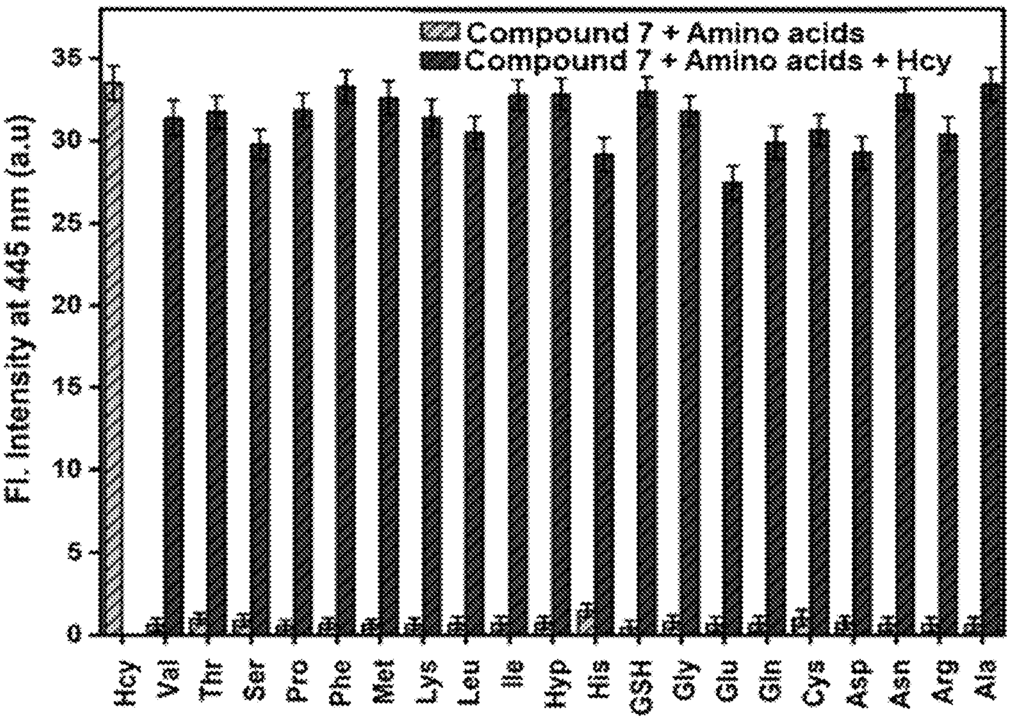
FIG. 12. Bar diagram showing selective fluorescence turn on responses of Compound 7 (20 μM in HEPES buffer) with Hcy (25 equivalent) in presence of equivalent amount of other competing amino acids.
Figure 13:
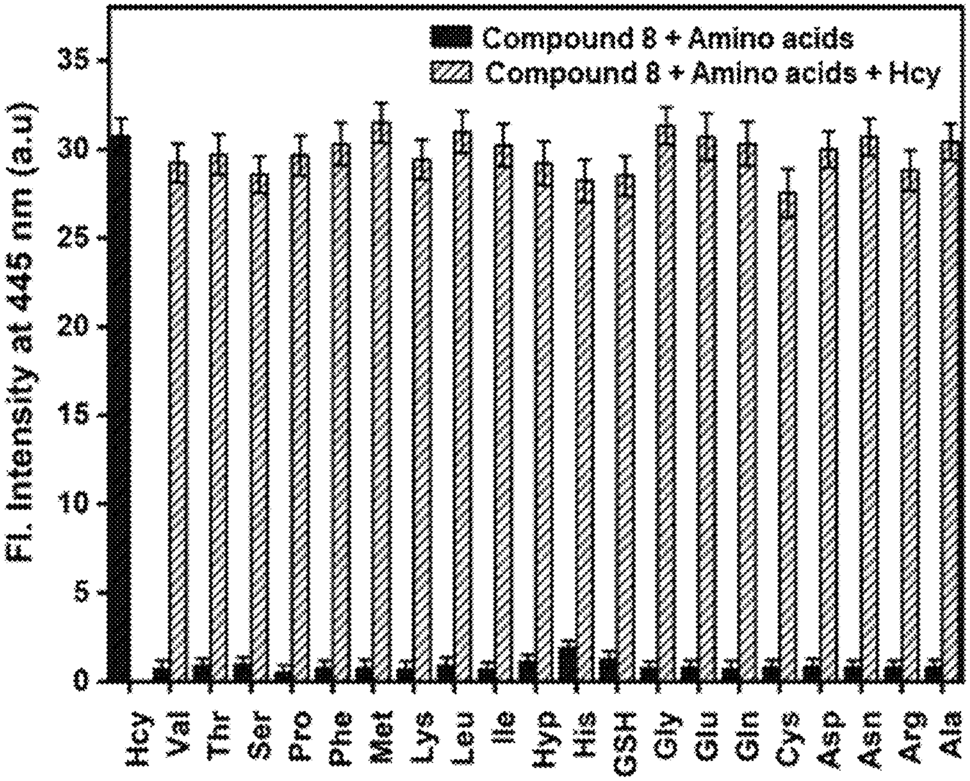
FIG. 13. Bar diagram showing selective fluorescence turn on responses of Compound 8 (20 μM in HEPES buffer) with Hcy (25 equivalent) in presence of equivalent amount of other competing amino acids.
Figure 14:
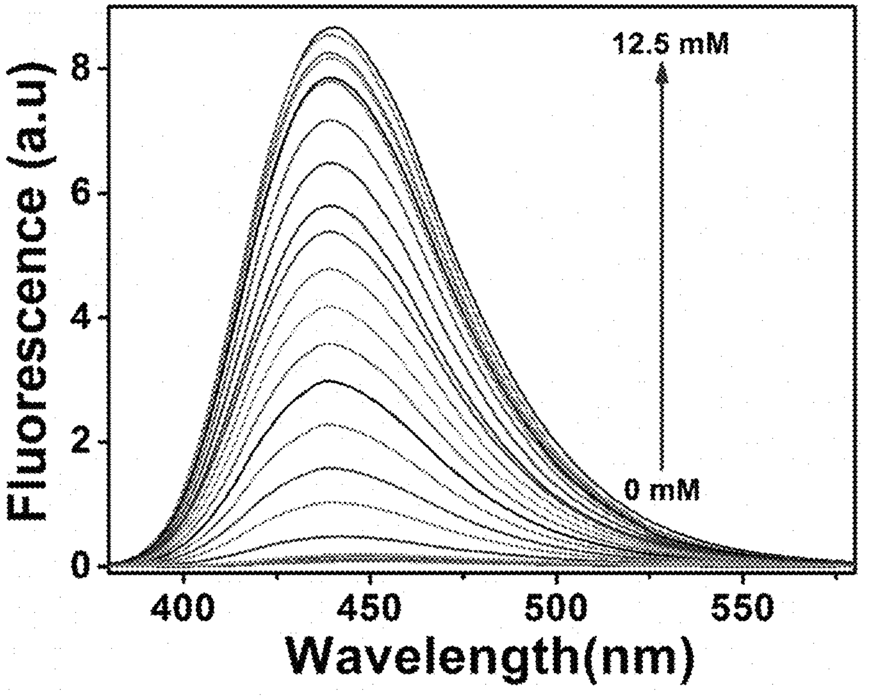
FIG. 14. Fluorimetric titration profiles for Compound 5 with increasing concentrations of Hcy at physiological pH 7.4.
Figure 15:
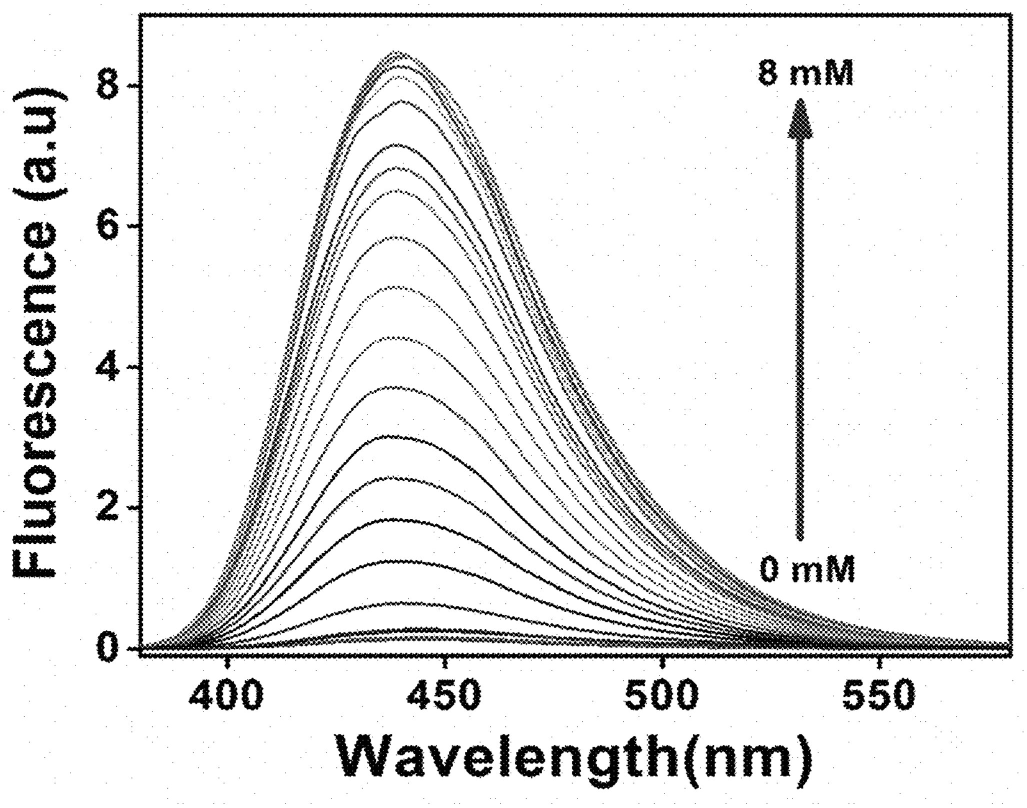
FIG. 15. Fluorimetric titration profiles for Compound 6 with increasing concentrations of Hcy at physiological pH 7.4.
Figure 16:
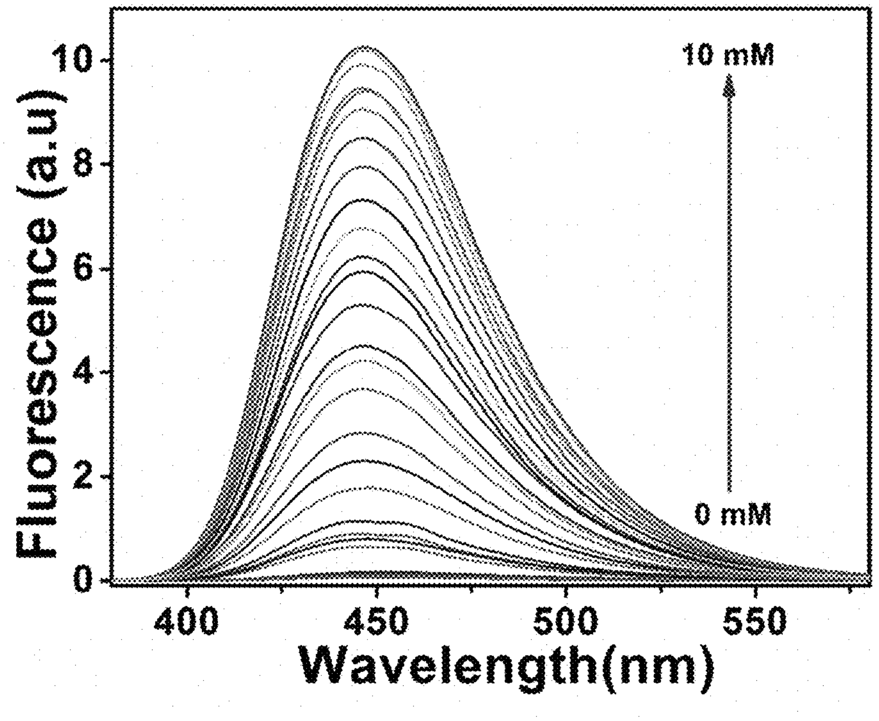
FIG. 16. Fluorimetric titration profiles for Compound 7 with increasing concentrations of Hcy at physiological pH 7.4.
Figure 17:
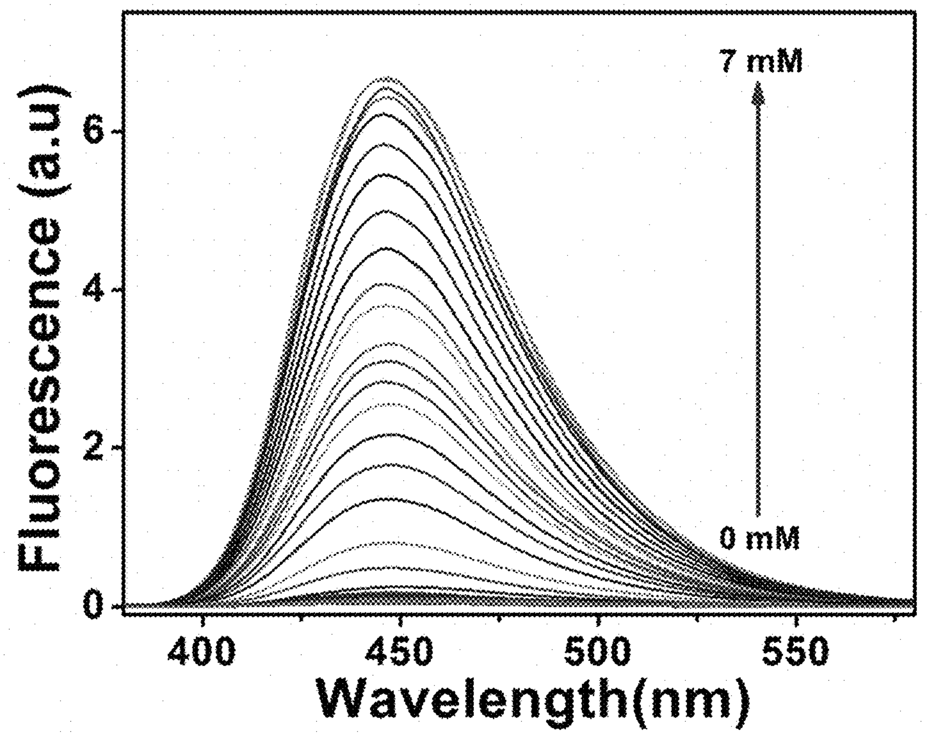
FIG. 17. Fluorimetric titration profiles for Compound 8 with increasing concentrations of Hcy at physiological pH 7.4.

The present invention discloses that the Compounds 5, 6, 7, and 8 are capable of detecting Hcy fluorimetrically among other competing amino acids like alanine, methionine, threonine, proline, leucine, isoleucine, lysine, phenylalanine, hydroxyproline, asparagine, argenine, serine, valine, cysteine, glutathione (reduced), glycine, histidine, and glutamine (FIG. 9).

Fluorescence based interference studies of Compound 5 to 8 in presence of other amino acids like alanine, methionine, threonine, proline, leucine, isoleucine, lysine, phenylalanine, hydroxyproline, asparagine, argenine, serine, valine, cysteine, glutathione (reduced), glycine, histidine, and glutamine showed no interference from other amino acids (FIGS. 10 to 13).

Figure 18:
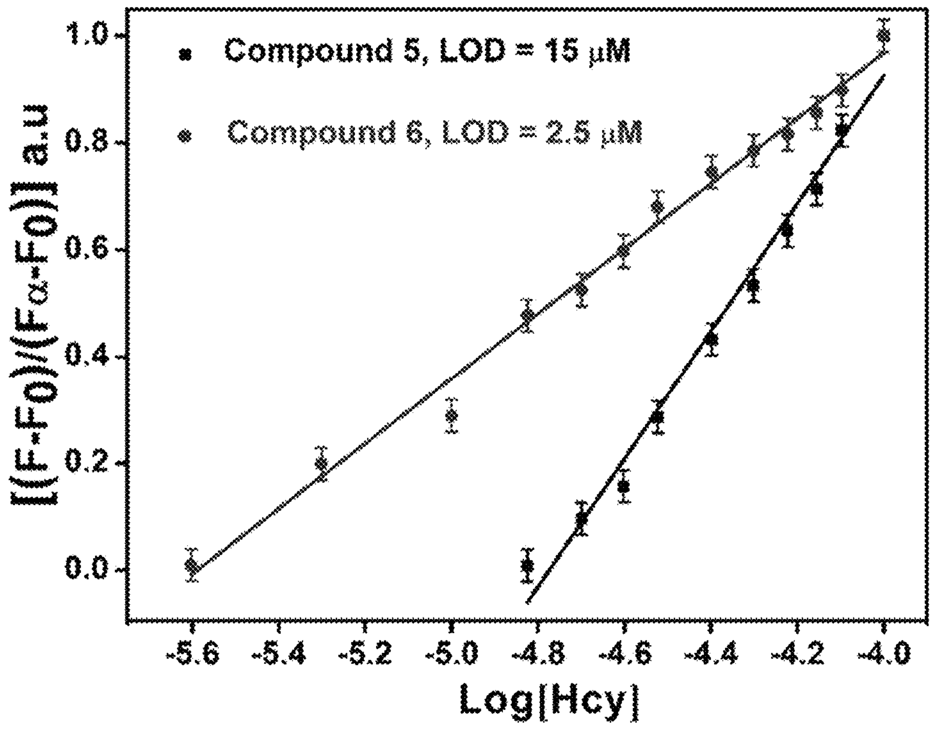
FIG. 18. Limit of detection (LOD) determination plots from fluorescence titration data of Compounds 5 and 6 in presence of different concentrations of Hcy.

As disclosed, the LODs for Hcy detection by the Compounds 5 and 6 are 15 and 2.5 μM, respectively (FIG. 18).

Figure 19:
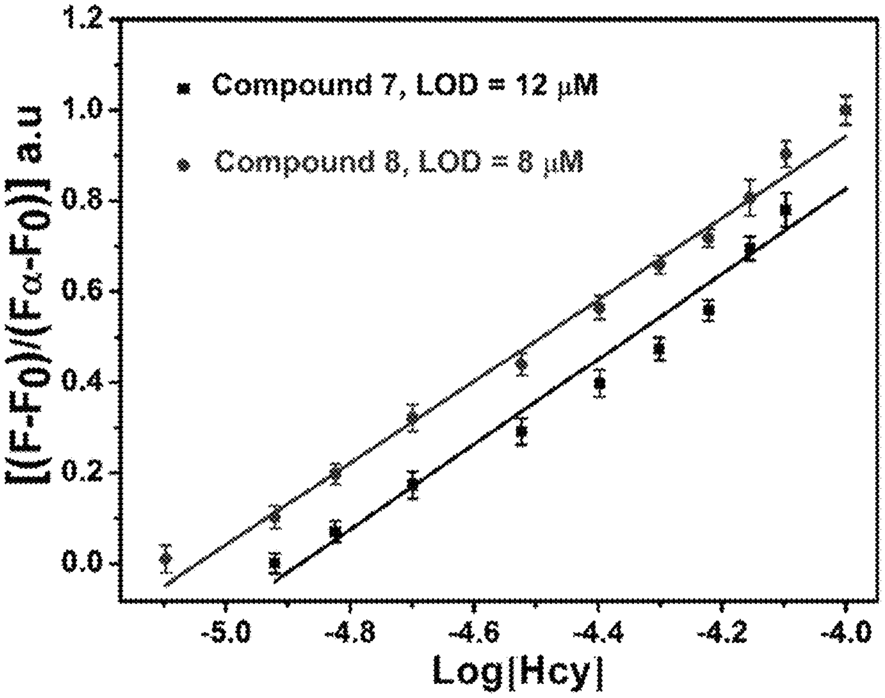
FIG. 19. Limit of detection (LOD) determination plots from fluorescence titration data of Compounds 7 and 8 in presence of different concentrations of Hcy.

As disclosed, the LODs for Hcy detection by the Compounds 7 and 8 are 12 and 8 μM, respectively (FIG. 19).

Figure 20:
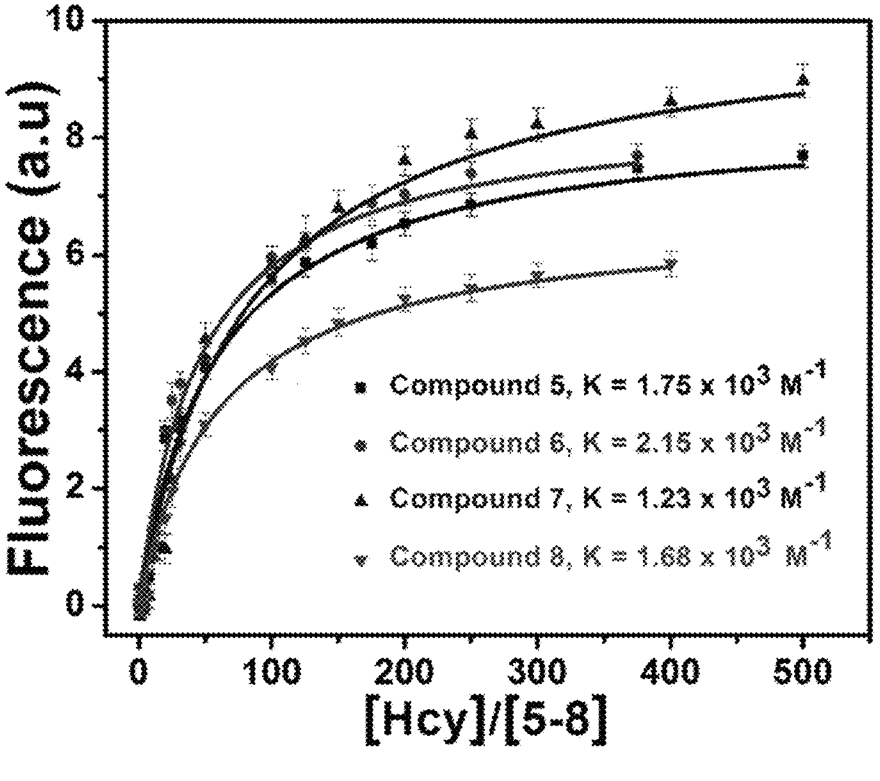
FIG. 20. Nonlinear fittings of the data points obtained from fluorescence titration of Compounds 5 to 8 in presence of varying concentrations of Hcy.
Figure 21:
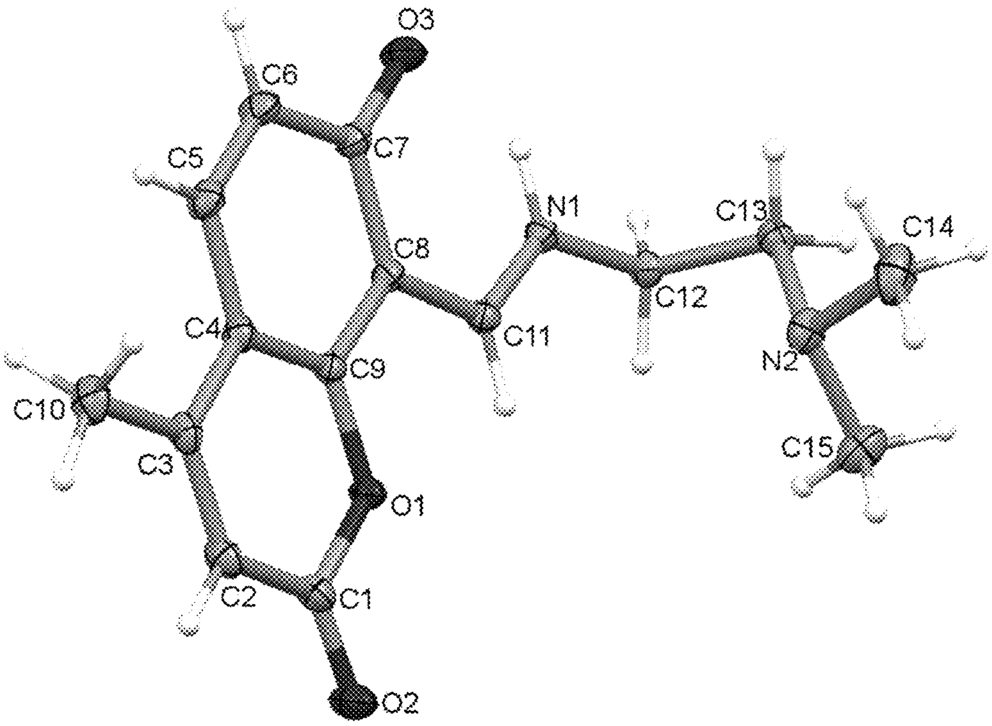
FIG. 21. Crystal structure of Compound 1.
Figure 22:
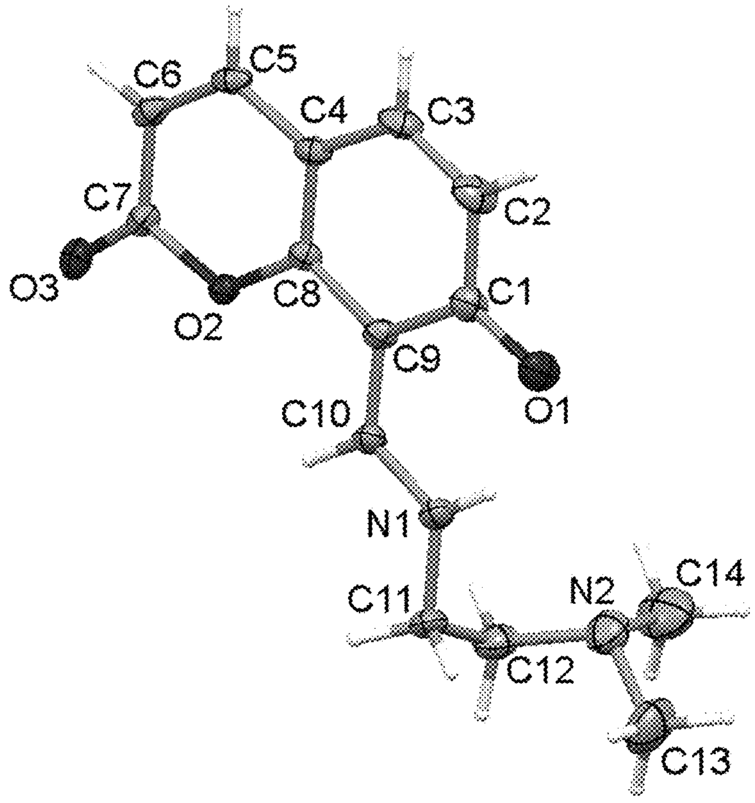
FIG. 22. Crystal structure of Compound 2.
Figure 23:
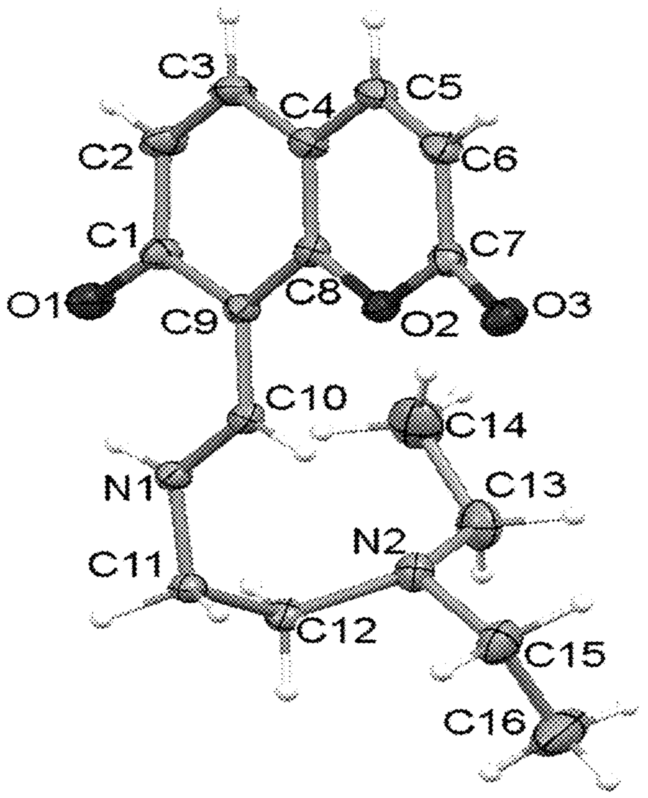
FIG. 23. Crystal structure of Compound 4.
Figure 24:
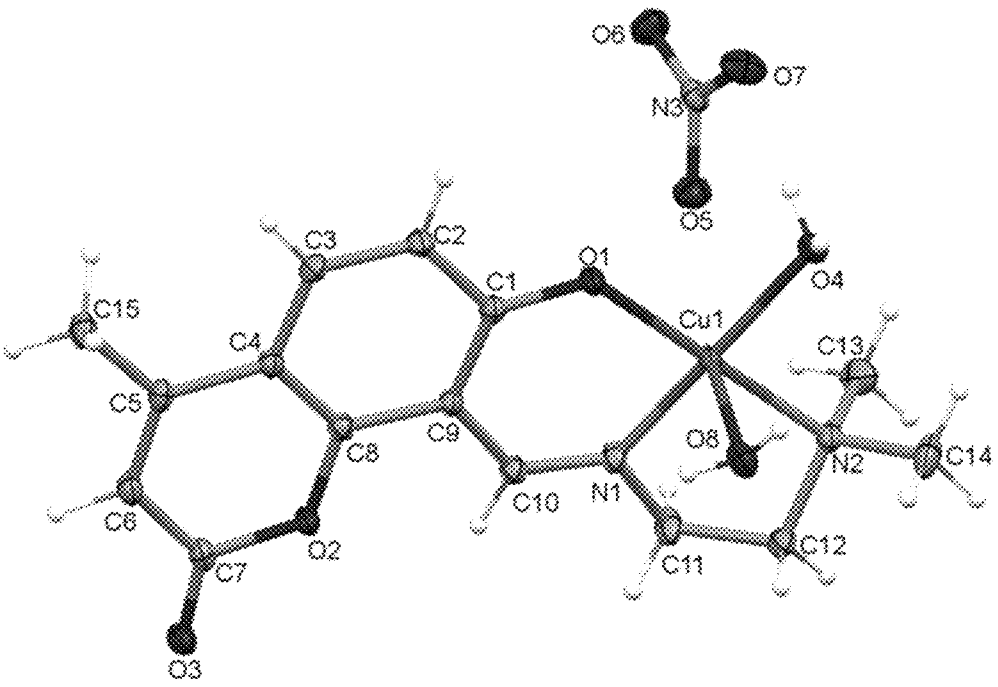
FIG. 24. Crystal structure of Compound 5.

Hcy concentration variable fluorescence titration data of Compounds 5, 6, 7, and 8 resulted the binding constants as $1.75\times10^3$ $M^{-1}$, $2.15\times10^3$ $M^{-1}$, $1.23\times10^3$ $M^{-1}$, and $1.68\times10^3$ $M^{-1}$, respectively (FIG. 20).

Materials and Physical Measurements

All chemicals were procured from Aldrich unless otherwise stated. All solvents were acquired from Finar and used without any further purification. 7-Hydroxy-4-methyl-2-oxo-2H-chromene-8-carbaldehyde and 7-Hydroxy-2-oxo-2H-chromene-8-carbaldehyde were prepared following the procedure described by Kamoto, M. et al. published in Chem.-Eur. J. 2008, 14, 8004-8012. The UV-vis spectra were recorded with Shimadzu 3600 UV-Vis-NIR spectrophotometer and Varian Cary-500 UV-Vis spectrophotometer. Elemental analyses (C, H, and N) were performed on an Elementar Vario MICRO CUBE analyser. Fluorescence experiments were performed on a Fluorolog FL 1065 Horiba Jobin Yvon Spectrometer instrument. IR spectra were recorded using Agilent Technologies Cary 600 Series spectrometer. pH of the solutions were measured using Thermo Scientific Orion Versa-star Advanced Electrochemistry meter at 298 K. JEOL Resonance ECZR 600 MHz spectrometer was used for $^1H$ and $^{13}C$ NMR spectra. The ESI-MS was measured on Micromass Q-ToF Micro™ and Agilent technologies 6545 Q-TOF LCMS/Infinity. The melting points of the ligands were measured using a Mettler-Toledo FP-62 instrument.

EXAMPLES

Following examples are given by way of illustration and therefore should not be construed to limit the scope of the invention.

Example 1: Preparation of Compound 1

8-(2-Dimethylamino)ethyliminomethyl-7-hydroxy-4-methyl-2H-chromen-2-one

Compound 1

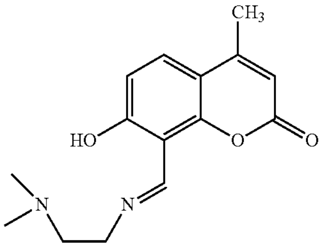

A mixture of 7-hydroxy-4-methyl-2-oxo-2H-chromene-8-carbaldehyde (204 mg, 1 mmol) and N,N-dimethylethylenediammine (88 mg, 1 mmol) in 1:1 stoichiometry was taken in a round bottom flask and 15 mL of methanol was added to this mixture. The mixture was refluxed under stirring for 3 h. TLC then monitored the progress of the reaction. After completion of the reaction, yellow solid was obtained after evaporating the solvent under pressure using rotary evaporator, Further, trituration with diethyl ether, the solid was collected and air dried further. Dried solid was then recrystallized using diethyl ether and further dried at room temperature to obtain the crystalline product.

Yield: 68% (recrystallized). MP: 157° C. $^1$H NMR ($CDCl_3$, 600 MHz, δ ppm)=14.83 (s, 1H, Phenolic O—H), 8.90 (s, 1H), 7.47 (d, 1H, J=9 Hz), 6.72 (d, 1H, J=9 Hz), 6.00 (s, 1H), 3.72 (t, 2H, J=6 Hz), 2.64 (t, 2H, J=6 Hz), 2.36 (s, 3H), 2.31 (s, 6H). $^{13}$C NMR ($CDCl_3$, 600 MHz, δ ppm)=19.04, 45.63, 52.67, 59.06, 104.89, 108.08, 109.05, 118.43, 130.02, 153.90, 155.44, 160.35, 160.82, 174.05. Anal. Calcd. for $C_{15}H_{18}N_2O_3$: C, 65.68; H, 6.61; N, 10.21. Found: C, 64.13; H, 6.4; N, 9.9. ESI-MS (+ive, m/z): 275.14 [M+H$^+$]. Selected IR bands (cm$^{-1}$): 3435, 2941, 2770, 1723, 1636, 1578, 1504, 1436, 1424, 1340, 1245, 1174, 1057, 834. UV-vis ($H_2O$) [$\lambda_{max}$, nm (ε, $L_{mol}{}^{-1}$ cm$^{-1}$)]: 350 (36000) and 277 (17400).

Example 2: Preparation of Compound 2

8-(2-Diethylamino)ethyliminomethyl-7-hydroxy-4-methyl-2H-chromen-2-one

Compound 2

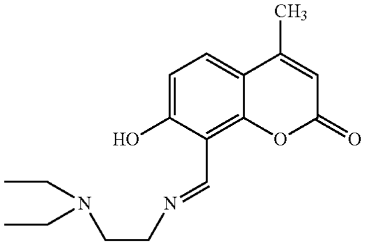

A mixture of 7-hydroxy-4-methyl-2-oxo-2H-chromene-8-carbaldehyde (204 mg, 1 mmol) and N,N-diethylethylenediammine (116 mg, 1 mmol) in 1:1 stoichiometry was taken in a round bottom flask and 15 mL of methanol was added to this mixture. The mixture was refluxed under stirring for 4 h. TLC monitored the progress of the reaction. After completion of the reaction, brownish yellow solid was obtained by the evaporation of the solvent under pressure using rotary evaporator. Yellow solid was obtained upon trituration with diethyl ether, which was air dried further. Solid was then recrystallized using diethyl ether and dried further at room temperature.

Yield: 62% (recrystallized). MP: 107° C. $^1$H NMR ($CDCl_3$, 600 MHz, δ ppm)=8.85 (s, 1H), 7.46 (d, 1H, J=9.6 Hz), 6.70 (d, 1H, J=9 Hz), 5.99 (s, 1H), 3.66 (t, 2H, J=6 Hz), 2.76 (t, 2H, J=6 Hz), 2.59 (q, 4H, J=7.2 Hz), 2.36 (s, 3H), 1.03 (t, 6H, J=7.2 Hz). $^{13}$C NMR ($CDCl_3$, 600 MHz, δ ppm)=12.03, 18.99, 47.31, 52.42, 52.70, 104.49, 107.46, 108.61, 119.08, 130.18, 153.94, 155.70, 160.25, 160.87, 175.42. Anal. Calcd. for $C_{17}H_{22}N_2O_3$: C, 67.53; H, 7.33; N, 9.26. Found: C, 66.47; H, 7.52; N, 9.17. ESI-MS (+ive, m/z): 303.17 [M+H$^+$]. Selected IR bands (cm$^{-1}$): 3431, 2967, 2931, 2864, 2798, 1735, 1720, 1644, 1585, 1507, 1433, 1380, 1184, 1066, 829. UV-vis ($H_2O$) [$\lambda_{max}$, nm (ε, Lmol$^{-1}$ cm$^{-1}$)]: 350 (40235) and 279 (20660).

Example 3: Preparation of Compound 3

8-(2-Dimethylamino)ethyliminomethyl-7-hydroxy-2H-chromen-2-one

Compound 3

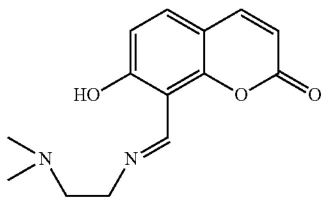

A mixture of 7-hydroxy-2-oxo-2H-chromene-8-carbaldehyde (204 mg, 1 mmol) and N,N-dimethylethylenediammine (88 mg, 1 mmol) in 1:1 stoichiometry was taken in a round bottom flask and 15 mL of methanol was added to this mixture. The mixture was refluxed under stirring for 3.5 h. TLC then monitored the progress of the reaction. After completion of the reaction, yellow solid was obtained after evaporating the solvent under pressure using rotary evaporator. So-obtained solid was further triturated with diethyl ether and then was collected and air-dried further. Solid was then recrystallized using diethyl ether to obtain crystalline product.

Yield: 68% (recrystallized). MP: 108° C. $^1$H NMR ($CDCl_3$, 600 MHz, δ ppm)=14.74 (s, 1H, Phenolic O—H), 8.86 (s, 1H), 7.56 (d, 1H, J=9. Hz), 7.31 (d, 1H, J=9 Hz), 6.69 (d, 1H, J=9 Hz), 6.11 (d, 1H, J=9.6 Hz), 3.72 (t, 2H, J=6 Hz), 2.65 (t, 2H, J=6 Hz), 2.31 (s, 6H). $^{13}$C NMR ($CDCl_3$, 600 MHz, δ ppm)=45.62, 52.28, 58.97, 104.79, 107.05, 109.59, 119.21, 133.43, 144.54, 156.40, 159.89, 160.90, 174.99. Anal. Calcd. for $C_{14}H_{16}N_2O_3$: C, 64.60; H, 6.20; N, 10.76. Found: C, 64.13; H, 6.21; N, 10.59. ESI-MS (+ive, m/z): 261.12 [M+H$^+$]. Selected JR bands (cm$^{-1}$): 3435, 2944, 2817, 2766, 1722, 1640, 1581, 1514, 1465, 1430, 1348, 1232, 1186, 1103, 994, 824. UV-vis ($H_2O$) [max, nm (ε, Lmol$^{-1}$ cm$^{-1}$)]: 353 (27250) and 277 (14200).

Example 4: Preparation of Compound 4 [$C_{16}H_{20}N_2O_3$]

8-(2-(Diethylamino)ethyliminomethyl-7-hydroxy-2H-chromen-2-one

Compound 4

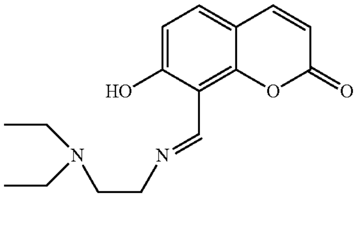

A mixture of 7-hydroxy-2-oxo-2H-chromene-8-carbaldehyde (190 mg, 1 mmol) and N,N-diethylethylenediamine (116 mg, 1 mmol) in 1:1 stoichiometry was taken in a round bottom flask and 15 mL of methanol was added to this mixture. The mixture was refluxed under stirring for 4 h. TLC then monitored the reaction mixture. After completion of the reaction, brown solid was obtained after evaporating the solvent under pressure using rotary evaporator, which was further triturated using diethyl ether. The solid was collected and air-dried further. Dried solid was then recrystallized using diethyl ether to obtain the crystalline product.

Yield: 62% (recrystallized). MP: 102° C. $^{1}H$ NMR ($CDCl_3$, 600 MHz, δ ppm)=14.60 (s, 1H, Phenolic O—H), 8.81 (s, 1H), 7.54 (d, 1H, J=9.6 Hz), 7.30 (d, 1H, J=9 Hz), 6.60 (d, 1H, J=9 Hz), 6.09 (d, 1H, J=9.6 Hz), 3.66 (t, 2H, J=6 Hz), 2.76 (t, 2H, J=6 Hz), 2.59 (q, 4H, J=7.2 Hz), 1.03 (t, 6H, J=7.2 Hz). $^{13}C$ NMR ($CDCl_3$, 600 MHz, δ ppm)=12.11, 47.36, 52.16, 52.75, 104.46, 106.52, 109.15, 119.88, 133.62, 144.60, 156.74, 159.84, 160.98, 176.35. Anal. Calcd. for $C_{16}H_{20}N_2O_3$: C, 66.65; H, 6.99; N, 9.72. Found: C, H, 7.22; N, 9.47. ESI-MS (+ive, m/z): 289.16 [$M+H^+$]. Selected IR bands ($cm^{-1}$): 3419, 2964, 2802, 1736, 1720, 1642, 1618, 1584, 1503, 1438, 1349, 1246, 1138, 1092, 981, 826. UV-vis ($H_2O$) [$\lambda_{max}$, nm (ε, $Lmol^{-1}$ $cm^{-1}$)]: 356 (21100) and 274 (8050).κ

Example 5: Preparation of Compound 5

Diaqua-8-(2-(dimethylamino)ethyliminomethyl-7-phenoxo-4-methyl-2H-chromen-2-onecopper(II) nitrate Compound 5

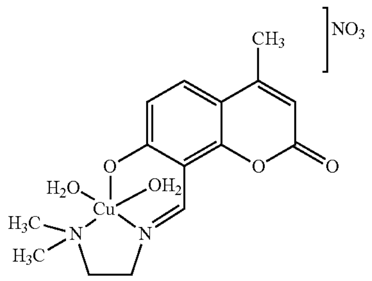

A mixture of copper nitrate trihydrate (241.6 mg, 1 mmol) and Compound 1 (274 mg, 1 mmol) in 1:1 stoichiometry was taken in a round bottom flask and 30 mL methanol was added to this mixture. The mixture was refluxed under stirring for ca. 3 h and TLC monitored the progress of the reaction. Green solid was obtained as precipitates after evaporating half of the solvent using rotary evaporator, which was further filtered to obtain the solid. The dried solid was recrystallized using methanol to obtain the pure product.

Yield: 60% (recrystallized). Selected IR bands ($cm^{-1}$): 3432, 2926, 1720, 1628, 1583, 1526, 1469, 1406, 1381, 1280, 1184, 1101, 1057, 1012, 836 and 775. Anal. Calcd. for $C_{15}H_{21}N_3O_8Cu$: C, 41.43; H, 4.87; N, 9.66. Found: C, 41.11; H, 5.02; N, 9.91. UV-vis ($H_2O$) [$\lambda_{max}$, nm (c, $Lmol^{-1}$ $cm^{-1}$)]: 410 (11050), 365 (21100), 332 (33000), 289 (36200), 257 (38100), 215 (67200).

Example 6: Preparation of Compound 6

Diaqua-8-(2-(diethylamino)ethyliminomethyl-7-phenoxo-4-methyl-2H-chromen-2-onecopper(II) nitrate Compound 6

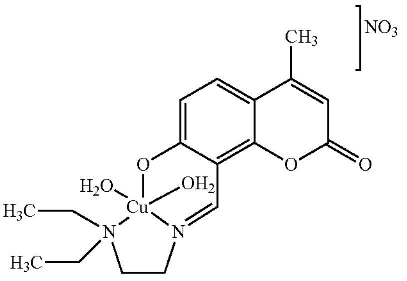

A mixture of copper nitrate trihydrate (241.6 mg, 1 mmol) and Compound 2 (302 mg, 1 mmol) in 1:1 stoichiometry was taken in a round bottom flask and 30 mL methanol was added to this mixture. The mixture was refluxed under stirring for ca. 3 h and TLC monitored the progress of the reaction. Green solid was obtained as precipitates after evaporating half of the solvent using rotary evaporator, which was further filtered to obtain the solid. The dried solid was further recrystallized using methanol to obtain the pure product.

Yield: 52% (recrystallized). Selected IR bands ($cm^{-1}$): 3423, 2976, 2938, 1730, 1630, 1581, 1530, 1476, 1403, 1338, 1286, 1189, 1100, 1060, 1011, 840, 772 and 740. Anal. Calcd. for $C_{17}H_{25}N_3O_8Cu$: C, 44.11; H, 5.44; N, 9.08. Found: C, 44.73; H, 5.32; N, 9.11. UV-vis ($H_2O$) [$\lambda_{max}$, nm (c, $Lmol^{-1}$ $cm^{-1}$)]: 418 (4800), 364 (14050), 339 (18500), 281 (18900), 211 (52450).

Example 7: Preparation of Compound 7

Diaqua-8-(2-(dimethylamino)ethyliminomethyl-7-phenoxo-2H-chromen-2-onecopper(II) nitrate Compound 7

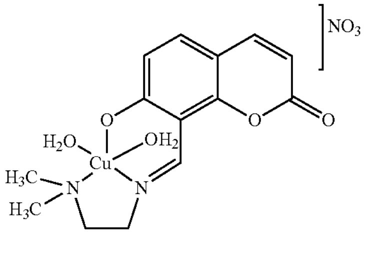

A mixture of copper nitrate trihydrate (241.6 mg, 1 mmol) and Compound 3 (260 mg, 1 mmol) in 1:1 stoichiometry was taken in a round bottom flask and 30 mL of methanol was added to this mixture. The mixture was refluxed under stirring for ca. 4 h and TLC monitored the progress of the reaction. Green solid was obtained by evaporating half of the solvent using rotary evaporator, which was filtered and the residue was dried in a desiccator. The dried solid was further recrystallized using methanol to obtain the pure product.

Yield: 51% (recrystallized). Selected IR bands ($cm^{-1}$): 3414, 3050, 2920, 1717, 1624, 1584, 1525, 1469, 1402, 1383, 1355, 1287, 1080, 1009, 838, 773. Anal. Calcd. for $C_{14}H_{19}N_3O_8Cu$: C, 39.95; H, 4.55; N, 9.98. Found: C, 40.39; H, 4.63; N, 10.11. UV-vis ($H_2O$) [$\lambda_{max}$, nm (c, $Lmol^{-1}$ $cm^{-1}$)]: 374 (18450), 350 (26800), 268 (23600), 248 (23000), 212 (62150).

Example 8: Preparation of Compound 8

Diaqua-8-(2-(diethylamino)ethyliminomethyl-7-phenoxo-2H-chromen-2-onecopper(II) nitrate Compound 8

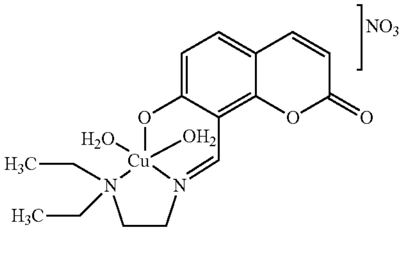

A mixture of copper nitrate trihydrate (241.6 mg, 1 mmol) and Compound 4 (288 mg, 1 mmol) in 1:1 stoichiometry was taken in a round bottom flask and 30 mL of methanol was added to this mixture. The reaction mixture was refluxed under stirring for ca. 3 h and TLC monitored the progress of the reaction. Green solid was obtained by evaporating half of the solvent using rotary evaporator. The solid was filtered and the residue was dried in a desiccator. The dried solid was further recrystallized using methanol to obtain the pure product.

Yield: 52% (recrystallized). Selected IR bands ($cm^{-1}$): 3428, 3061, 2975, 2920, 1732, 1630, 1587, 1525, 1469, 1410, 1386, 1287, 1072, 1009, 832, 773. Anal. Calcd. for $C_{16}H_{23}N_3O_8Cu$: C, 42.81; H, 5.16; N, 9.36. Found: C, 42.57; H, 5.23; N, 9.11. UV-vis ($H_2O$) [$\lambda_{max}$, nm (c, $Lmol^{-1}$ $cm^{-1}$)]: 432 (8400), 372 (14400), 347 (20350), 273 (20150), 244 (17800), 211 (47950).

Advantages of the Invention

Elevated homocysteine levels in human plasma refers to a health condition known as hyperhomocysteinemia, which is connected to the early onset of several critical health illnesses and age related pathologies. Despite tens of thousands of publications in the literature on the relationship between the acute health disorders and homocysteine levels, we are not aware of any clinically tested optical assay for direct measurement of homocysteine in human blood. To manage various clinical pathologies, simple and rapid measurement of plasma homocysteine at the early stage is indispensable. Several analytical methods including HPLC, GCMS, CE, voltammetry, and ELISA have been developed as techniques for measuring Hcy. Even though some of these techniques are useful, most of these methods suffer from the disadvantages of the use of very expensive instruments, tedious procedures, requirement of skilled person to handle the sophisticated instruments, and complicated pre-treatment of samples to make them unsuitable for routine detection in diagnostic laboratory. There is no optical kit available in India to measure Hcy directly. The cost per test for indirect measurement of Hcy (which is enzyme based immunoassay) ranges within Rs. 1500-2500. Optical probes, which are soluble in aqueous media, are highly preferred for biological applications but most of the available or reported probes require organic solvent as co-solvent for the detection purposes. In this context, Compounds of Formula B (i.e. Compounds 5-8) are cost effective and wateraqueous soluble. Therefore, entire analysis can be performed in non-organic medium. Since homocysteine is a homologue of cysteine, differing only by an additional methylene moiety, selective detection/measurement of the former in human blood plasma is a very challenging task because of the interference from cysteine (cys) and glutathione (GSH). Compounds of Formula B can detect homocysteine directly and selectively, even in presence of cysteine and glutathione. The results obtained with the Compounds of Formula B showed excellent correlation with gold standard techniques. These promising results apparently concludes that Compounds of Formula B have the potential to be used as diagnostic kit for routine analysis and prognosis for cardiac patients in clinical laboratories with minimal resource settings.

We claim:

1. A compound of Formula-B

Formula-B

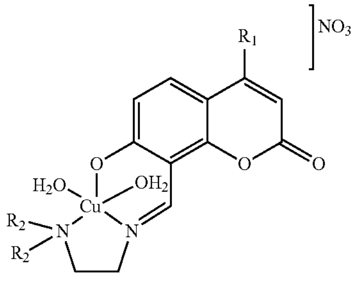

wherein $R_1$=—$CH_3$ or —H and $R_2$=—$CH_3$ or —$C_2H_5$.

2. The compound as claimed in claim 1, wherein the compound of Formula-B is selected from the group consisting of:

(i) [Diaqua-8-(2-dimethylamino)ethylethylminomethyl-7-phenoxo-4-methyl-2H-chromen-2-onecopper(II) nitrate]

Compound 5

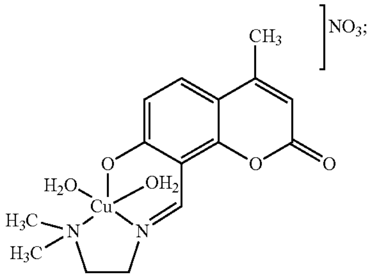

(ii) [Diaqua-8-(2-(diethylamino)ethyliminomethyl-7-phenoxo-4-methyl-2H-chromen-2-onecopper(II) nitrate]

Compound 6

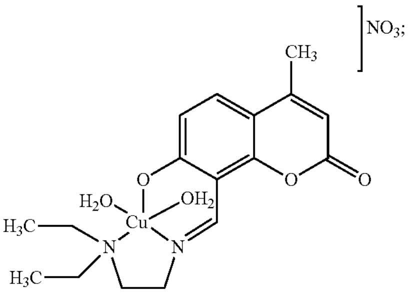

(iii) [Diaqua-8-(2-(dimethylamino)ethyliminomethyl-7-phenoxo-2H-chromen-2-onecopper(II) nitrate]

Compound 7

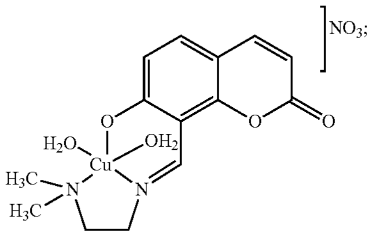

and (iv) [Diaqua-8-(2-(diethylamino)ethyliminomethyl-7-phenoxo-4-2H-chromen-2-onecopper(II) nitrate]

Compound 8

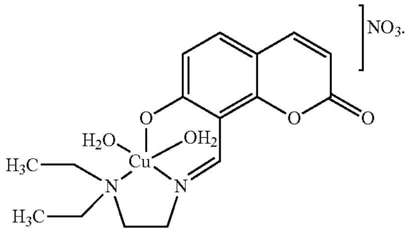

3. The compound as claimed in claim 1, wherein said compound is used for a fluorimetric measurement of Hcy in aqueous solution at physiological pH, even in presence of other competing species selected from the group consisting of alanine, methionine, threonine, proline, leucine, isoleucine, lysine, phenylalanine, hydroxyproline, asparagine, arginine, serine, valine, cysteine, glutathione, glycine, histidine, glutamine and combination thereof.

4. A process for preparation of the compound of Formula-B

Formula-B

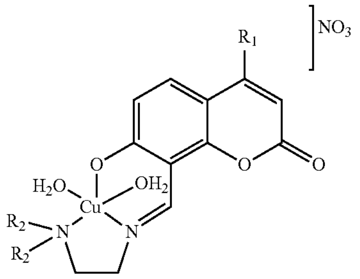

wherein $R_1$=—$CH_3$ or —H and $R_2$=—$CH_3$ or —$C_2H_5$, comprising the steps of:

(i) refluxing a mixture of 7-Hydroxy-4-methyl-2-oxo-2H-chromene-8-carbaldehyde or 7-Hydroxy-2-oxo-2H-chromene-8-carbaldehyde and N,N-dimethylethylenediamine or N,N-diethylethylenediamine in a stoichiometry ratio 1:1 in a solvent for a period in the range of 3-4 h followed by evaporating the solvent to obtain a residue;

(ii) triturating the residue as obtained in step (i) with diethyl ether to obtain a yellow solid;

(iii) recrystallizing the solid as obtained in step (ii) to obtain crystalline Compound of Formula-A;

Formula-A

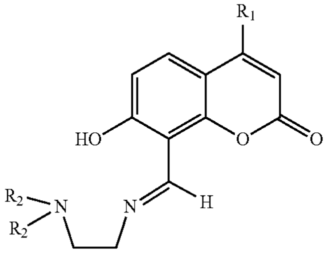

(iv) refluxing a mixture of copper salt and compound of Formula-A in 1:1 stoichiometry in a solvent for a period in the range of 3-4 h followed by evaporating the solvent to obtain green coloured solid;

(v) filtering the green coloured solid as obtained in step (i) followed by drying to obtain a solid; and (vi) recrystallizing the solid as obtained in step (ii) to obtain compound of Formula-B in pure form.

5. The process as claimed in claim 4, wherein compound of Formula-A is selected from the group consisting of:

(i) [8-(2-(Dimethylamino)ethyl)minomethyl)-7-hydroxy-4-methyl-2H-chromen-2-one]

Compound 1

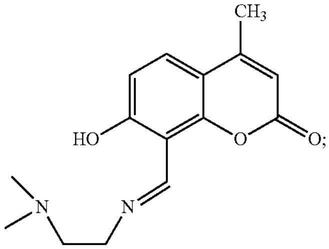

(ii) [8-(2-(Diethylamino)ethyliminomethyl-7-hydroxy-4-methyl-2H-chromen-2-one

Compound 2

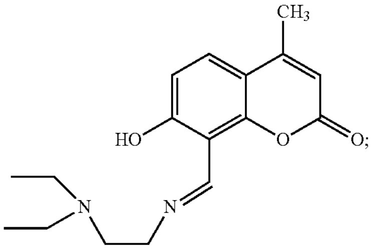

(iii) [8-(2-(Dimethylamino)ethyliminomethyl-7-hydroxy-2H-chromen-2-one]

Compound 3

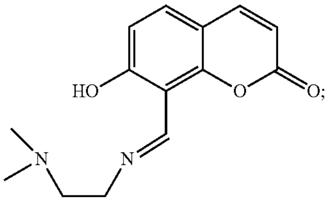

and (iv) [8-(2-(Diethylamino)ethyliminomethyl-7-hydroxy-2H-chromen-2-one]

Compound 4

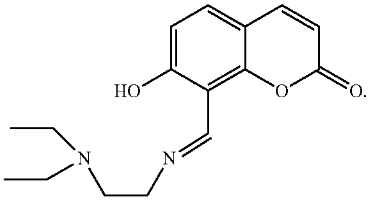

6. The process as claimed in claim 4, wherein the solvent is selected from methanol or acetonitrile.

7. The process as claimed in claim 4, wherein the copper salt is selected from the group consisting of copper nitrate trihydrate, copper halide, copper perchlorate and copper acetate.

* * * * *